(12) United States Patent
Anazawa et al.

(10) Patent No.: US 11,391,694 B2
(45) Date of Patent: Jul. 19, 2022

(54) PISTON AND SYRINGE

(71) Applicant: Hitachi High-Tech Corporation, Tokyo (JP)

(72) Inventors: Takashi Anazawa, Tokyo (JP); Kunio Harada, Tokyo (JP); Motohiro Yamazaki, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 323 days.

(21) Appl. No.: 16/755,069

(22) PCT Filed: Oct. 9, 2018

(86) PCT No.: PCT/JP2018/037547
§ 371 (c)(1),
(2) Date: Apr. 9, 2020

(87) PCT Pub. No.: WO2019/073955
PCT Pub. Date: Apr. 18, 2019

(65) Prior Publication Data
US 2021/0190725 A1   Jun. 24, 2021

(30) Foreign Application Priority Data
Oct. 12, 2017 (JP) .............................. JP2017-198877

(51) Int. Cl.
*G01N 27/447* (2006.01)
(52) U.S. Cl.
CPC .............................. *G01N 27/44743* (2013.01)
(58) Field of Classification Search
CPC ....... G01N 27/44743; G01N 2030/185; G01N 1/00; G01N 27/44704; A61M 5/315
See application file for complete search history.

(56) References Cited

U.S. PATENT DOCUMENTS

| 4,986,820 A | 1/1991 | Fischer |
| 7,087,037 B2 | 8/2006 | Chiba et al. |
| (Continued) | | |

FOREIGN PATENT DOCUMENTS

| JP | 2001-029469 A | 2/2001 |
| JP | 2001-259032 A | 9/2001 |
| (Continued) | | |

OTHER PUBLICATIONS

International Search Report and Written Opinion for related International Application No. PCT/JP2018/037547, dated Nov. 13, 2018; English translation of ISR provided (8 pages).

*Primary Examiner* — Jennifer Wecker
*Assistant Examiner* — Oyeleye Alexander Alabi
(74) *Attorney, Agent, or Firm* — Procopio, Cory, Hargreaves & Savitch LLP

(57) ABSTRACT

In order to provide a piston and a syringe with good sliding performance and pressure resistance performance, the piston contained in the syringe that pressurizes or decompresses an internal medium is configured such that a soft portion made of a soft material and a rigid portion made of a material having rigidity higher than rigidity of the soft portion, are connected in series, and arranged such that the soft portion is in contact with the medium and the rigid portion is not in contact with the medium. The soft portion includes a hollow on a surface in contact with the medium. The rigid portion has an end surface facing the soft portion, the end surface including at least an outer peripheral portion in contact with the soft portion. The outer diameter of the soft portion is larger than the outer diameter of the rigid portion, and the outer diameter of the rigid portion is slightly smaller than the inner diameter of an outer cylinder of the syringe.

14 Claims, 28 Drawing Sheets

(56) References Cited

U.S. PATENT DOCUMENTS

| | | | |
|---|---|---|---|
| 2003/0014005 A1 | 1/2003 | Chiba et al. | |
| 2003/0065291 A1* | 4/2003 | Corrigan, Jr. | A61M 5/3135 604/199 |
| 2007/0060896 A1 | 3/2007 | Miller et al. | |

FOREIGN PATENT DOCUMENTS

| | | |
|---|---|---|
| JP | 2009-505794 A | 2/2009 |
| JP | 4558130 B2 | 10/2010 |

\* cited by examiner

FIG. 9A  COMPARATIVE EXAMPLE A
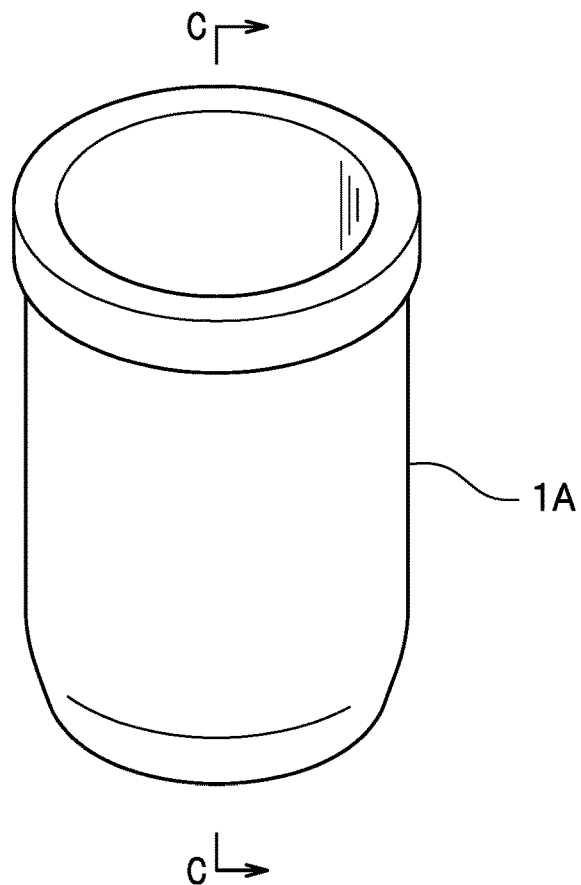
FIG. 9B  COMPARATIVE EXAMPLE A
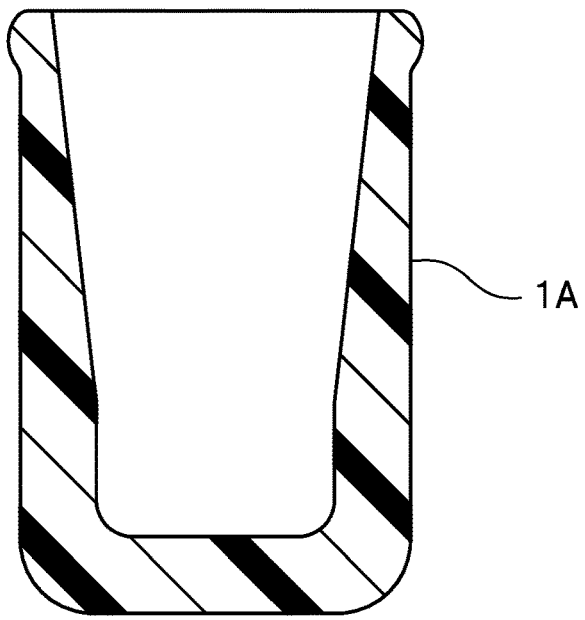

COMPARATIVE EXAMPLE D

COMPARATIVE EXAMPLE D

COMPARATIVE EXAMPLE D

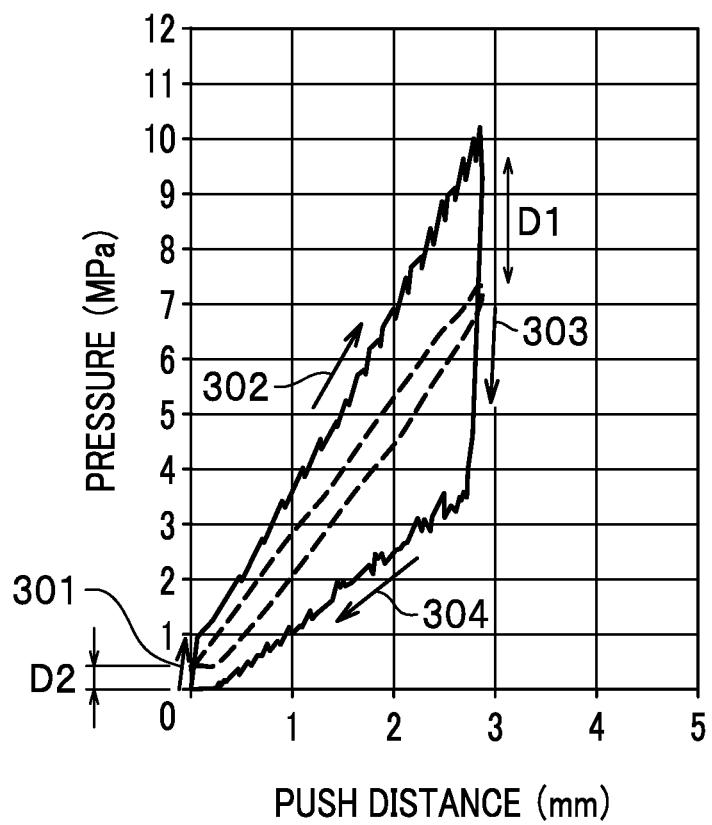
FIG. 11A  COMPARATIVE EXAMPLE A

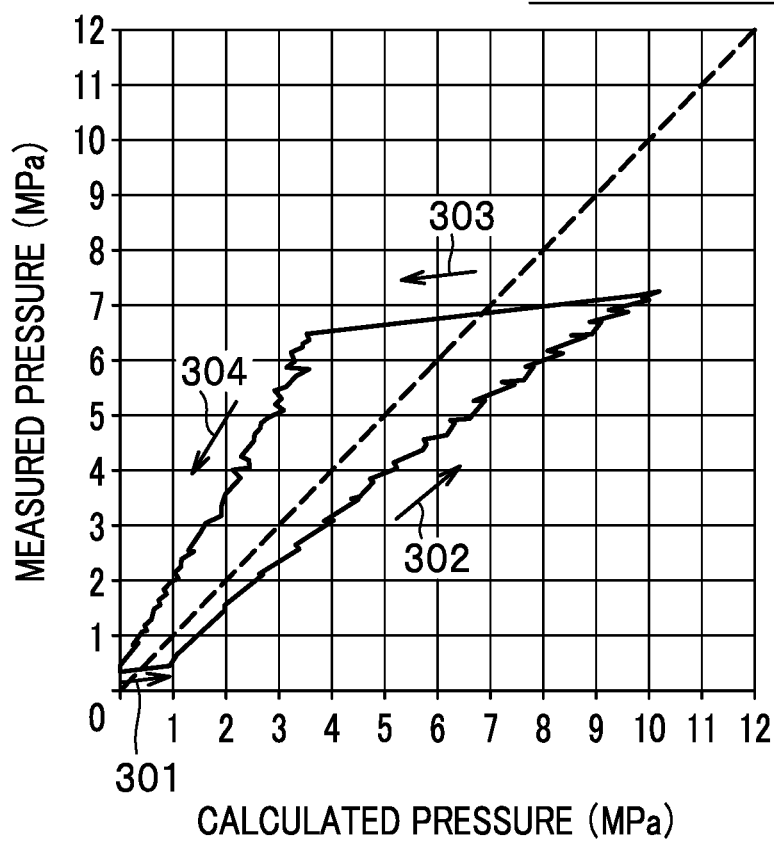
FIG. 11B  COMPARATIVE EXAMPLE A

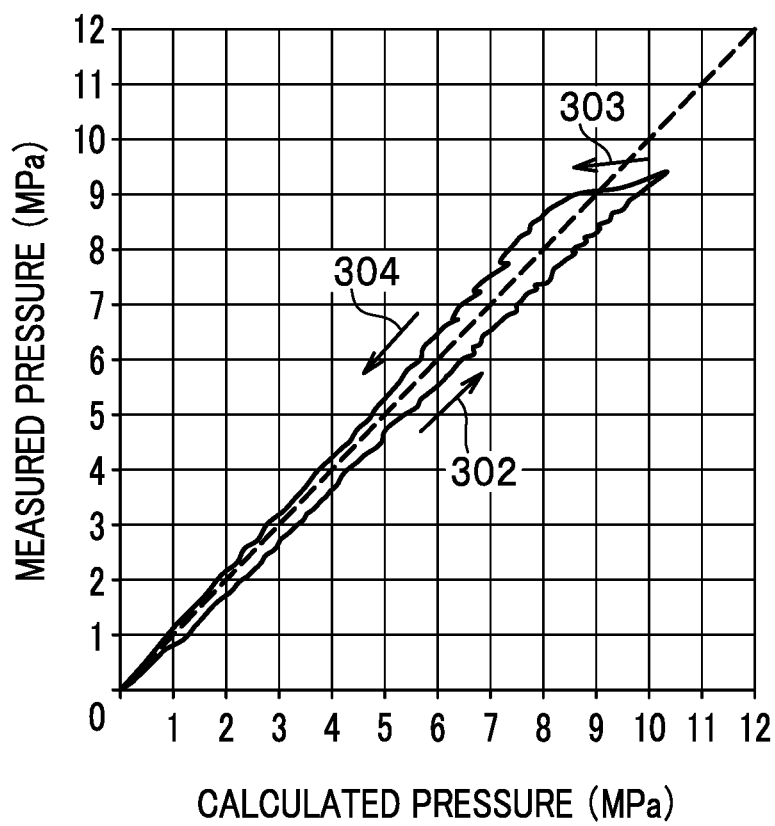

FIG. 14A  COMPARATIVE EXAMPLE B
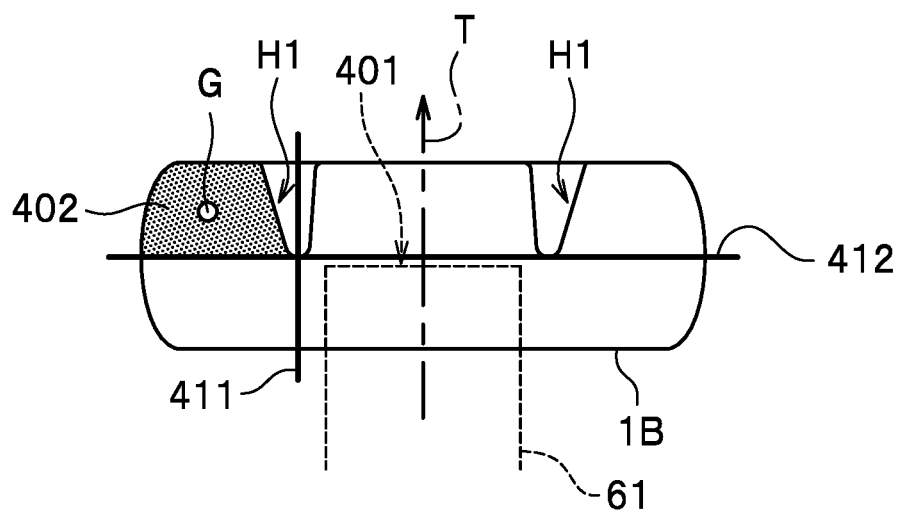
FIG. 14B  COMPARATIVE EXAMPLE B
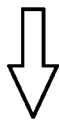
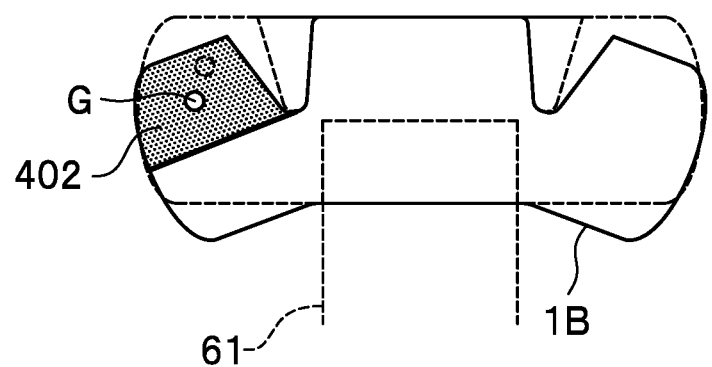

FIG. 15A   COMPARATIVE EXAMPLE C
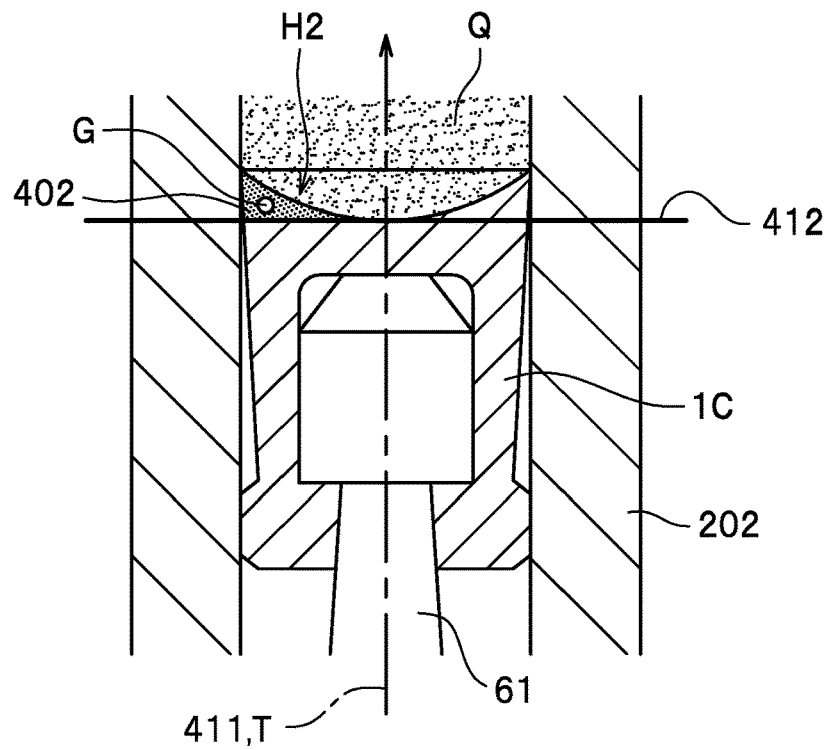
FIG. 15B   COMPARATIVE EXAMPLE C
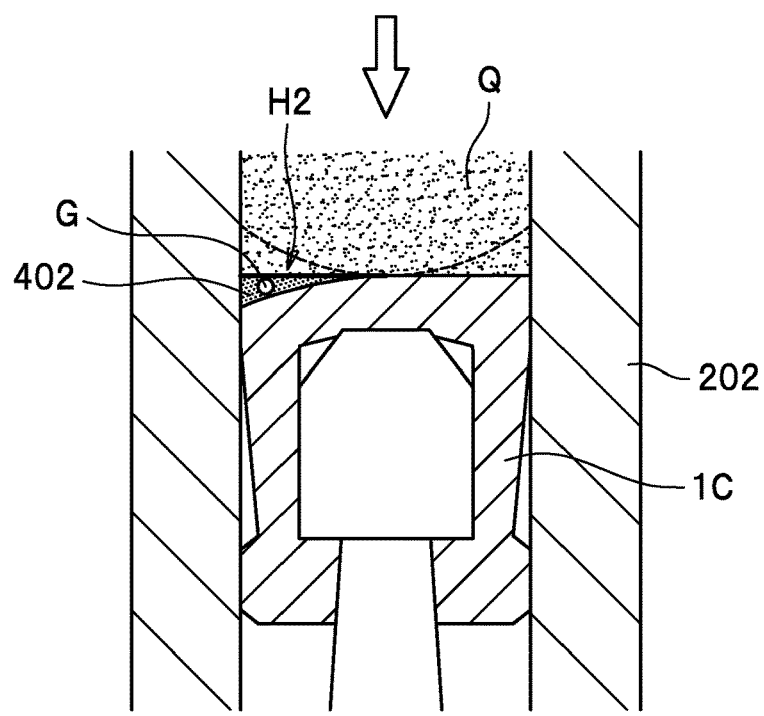

FIG. 17A    COMPARATIVE EXAMPLE B
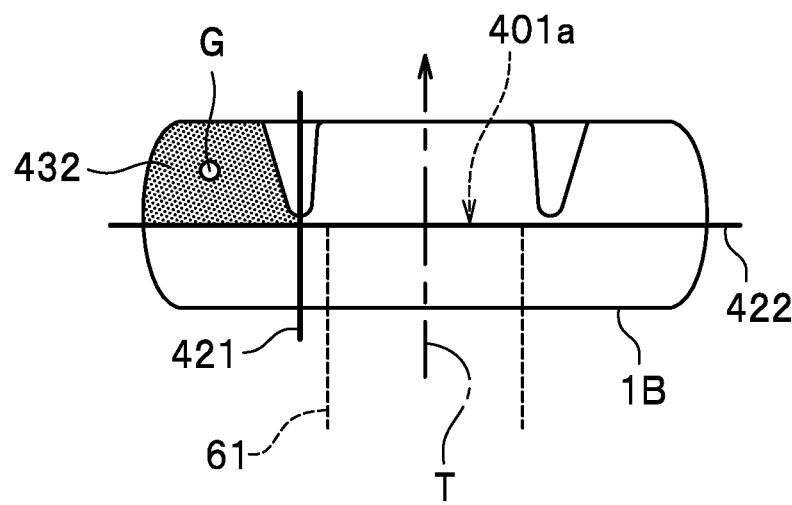
FIG. 17B    COMPARATIVE EXAMPLE B
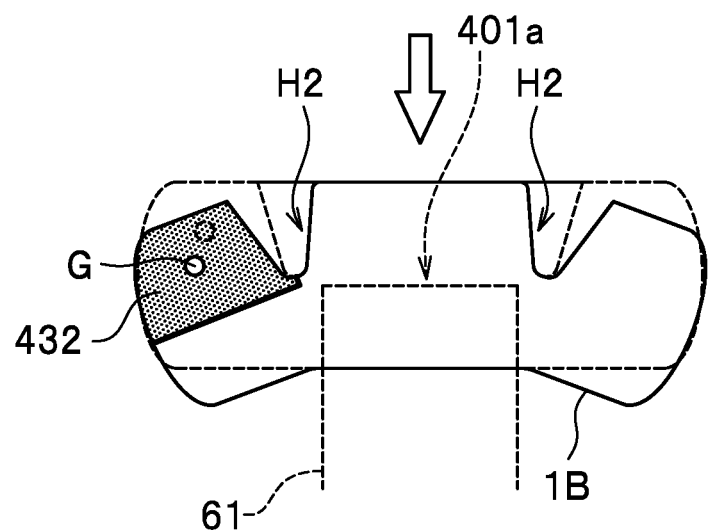

FIG. 18A   COMPARATIVE EXAMPLE C
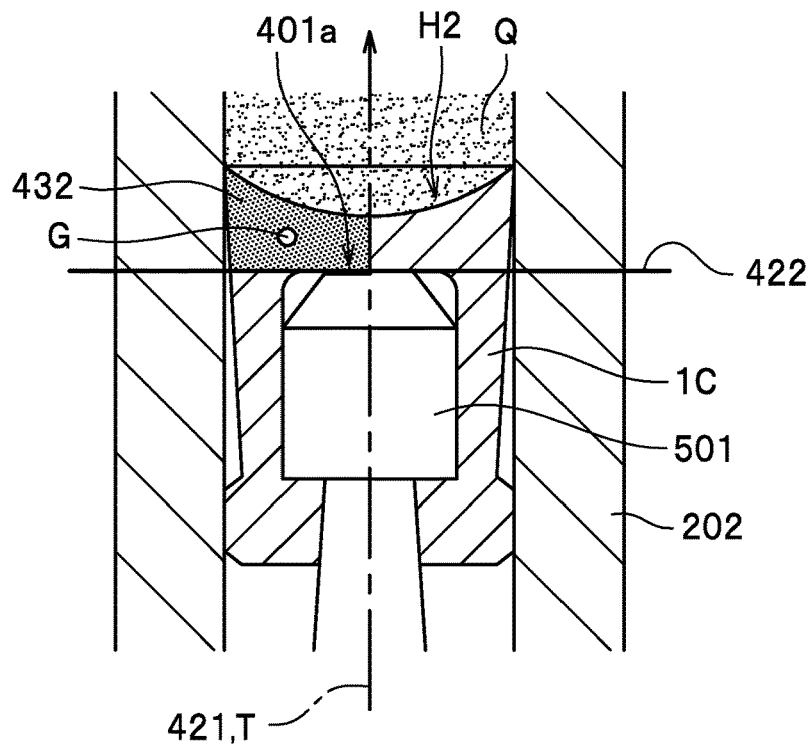
FIG. 18B   COMPARATIVE EXAMPLE C
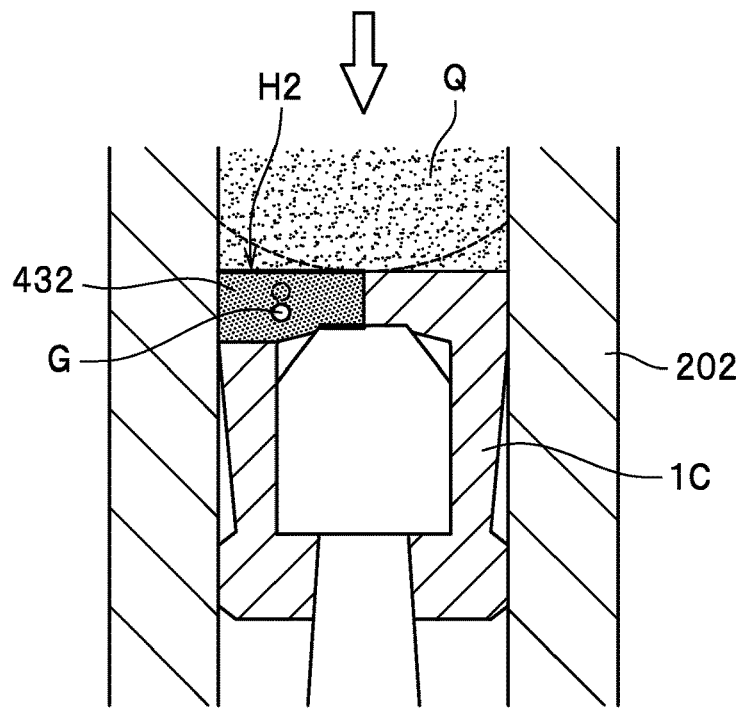

FIG. 19
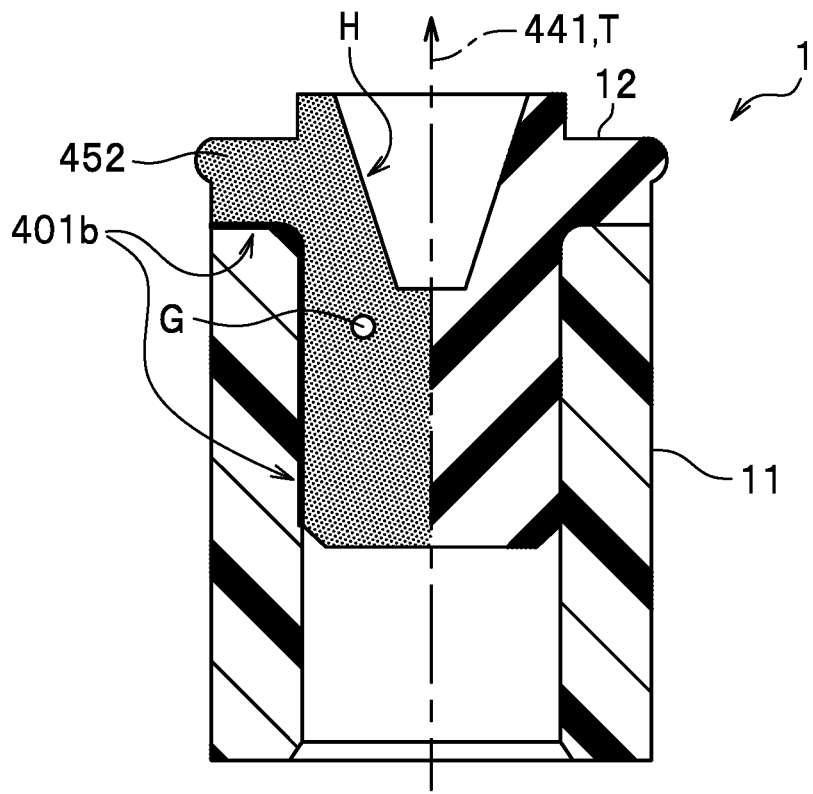
FIG. 20    COMPARATIVE EXAMPLE B
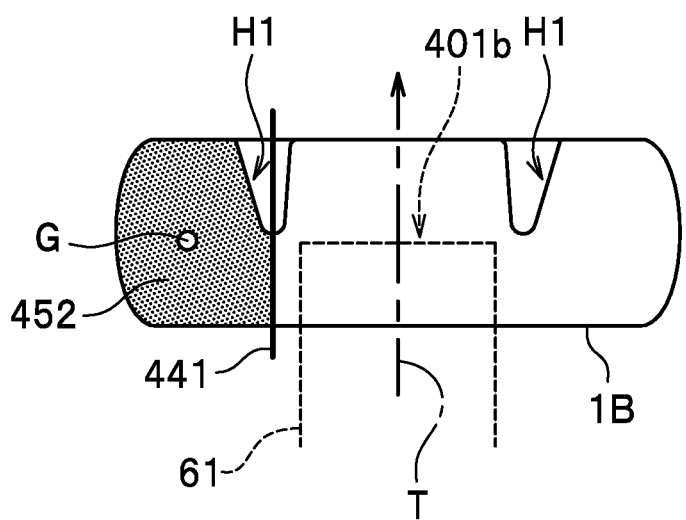

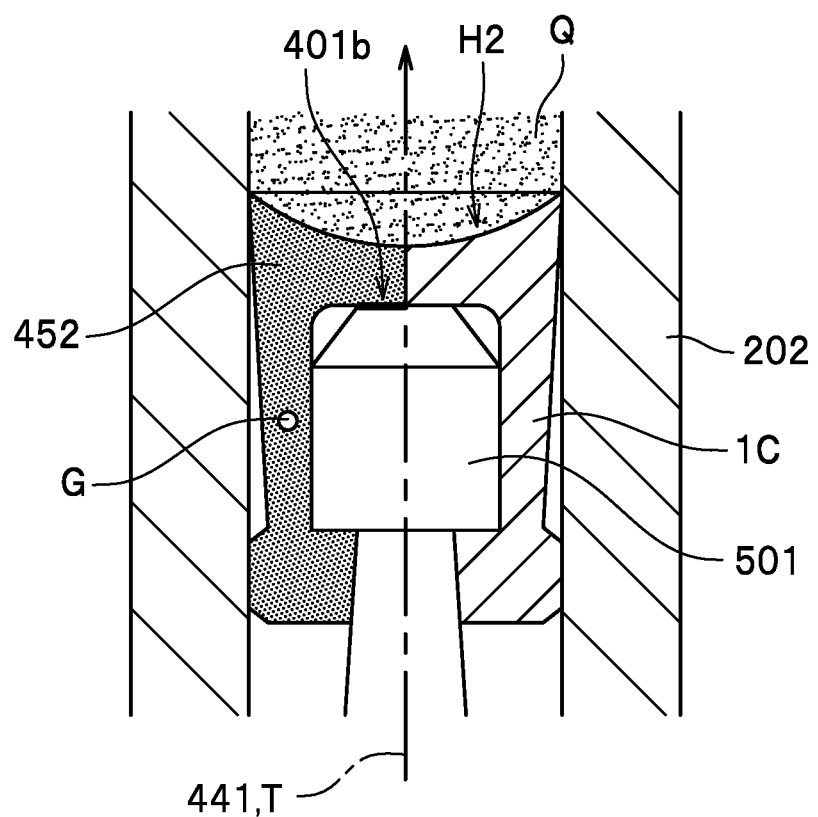
FIG. 21  COMPARATIVE EXAMPLE C

FIG.22A
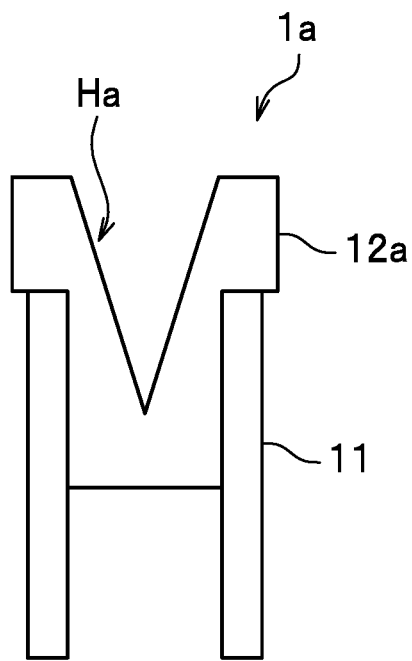
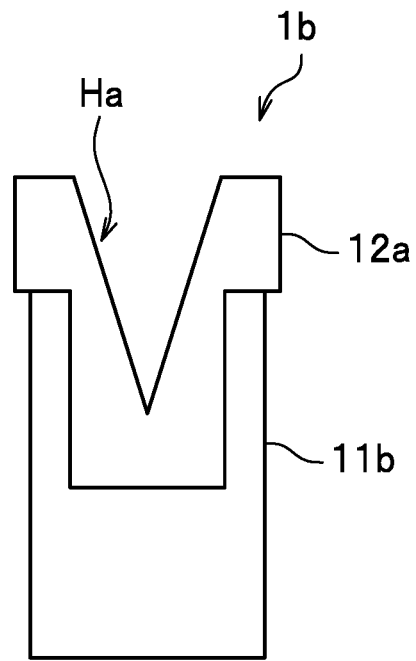
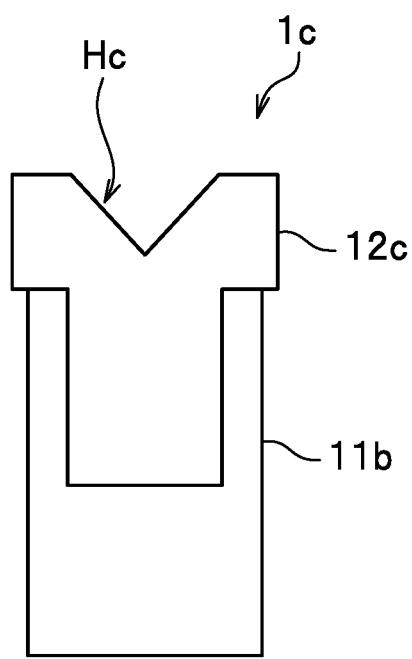
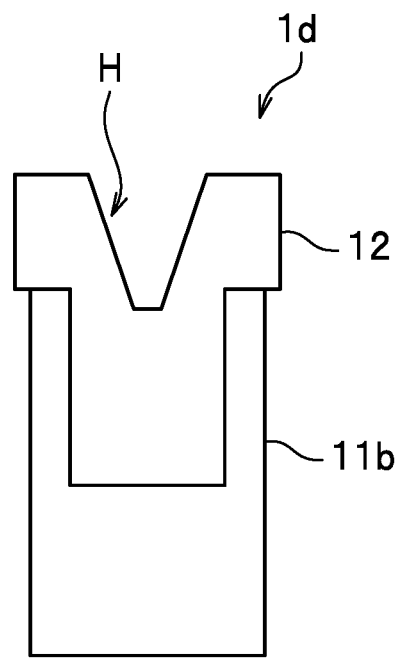

US 11,391,694 B2

PISTON AND SYRINGE

CROSS-REFERENCE TO RELATED APPLICATIONS

This application is a U.S. National Stage entry of PCT Application No: PCT/JP2018/037547 filed Oct. 9, 2018, which claims priority to Japanese Patent Application No. 2017-198877, filed Oct. 12, 2017, the contents of which are incorporated herein by reference.

TECHNICAL FIELD

The present invention relates to technology for a piston and a syringe.

BACKGROUND ART

In recent years, capillary electrophoresis devices in which capillaries are filled with an electrophoresis medium such as a polymer gel or a polymer solution have been widely used as electrophoresis apparatuses. When filling the capillaries with the electrophoresis medium, a syringe is used. In a case where the viscosity of the electrophoresis medium is high, it is necessary to apply a high pressure to the electrophoresis medium inside the syringe. Therefore, a high sealing performance (a high pressure resistance performance) is required between the syringe and the piston.

In Patent Document 1, the piston has a recess provided at the tip thereof. In the disclosure, the tip of the piston is pushed to be widened in the radially outside direction of the syringe as the pressure increases. This improves the sealing performance between the tip of the piston and the inner wall of the syringe when the high pressure is applied.

Patent Document 2 discloses "an injector comprising a barrel for mounting an injection needle thereon and a plunger with a gasket joined to a tip end thereof and held in intimate sliding contact with an inner wall surface of the barrel, said gasket being of substantial plate-shape, an entire side surface thereof being a curved surface having a convex-shaped arc rising in the direction of the inner wall surface of the barrel and extending along an axis direction of the plunger, and being held in intimate contact with the inner wall surface of the barrel at a portion of the curved surface thereof, said gasket being joined to a mount base disposed on a tip end of the plunger and smaller in diameter than the tip end of the plunger with a gap left to be bendable toward the tip end of the plunger, said gasket having an annular groove defined in a surface thereof remote from said plunger and larger in diameter than said mount base and provided at a depth to an intermediate position in the thickness direction of the gasket, said gasket having a bendable portion in a portion thereof disposed radially outwardly of said annular groove, which bends about a bottom of said annular groove toward an axis of the plunger radially outwardly of said mount base when the gasket is held in intimate contact with an inner wall surface of the barrel and slides toward a tip end of the barrel, said bendable portion being formed so that a distance between the bottom of said annular groove and a crest of said curved surface being smaller than a radius of curvature of said curved surface." (See claim 1). Herein, the gasket, plunger and injector in Patent Document 2 correspond to the piston, plunger and syringe in the embodiment, respectively.

CITATION LIST

Patent Document

Patent Document 1: U.S. Pat. No. 4,986,820
Patent Document 2: JP 4558130 B1

SUMMARY OF INVENTION

Technical Problem

A syringe used in a capillary electrophoresis device may be subjected to a very high pressure of about 10 MPa. Therefore, the syringe used in the capillary electrophoresis device is required to have high pressure resistance performance. Further, a syringe used in the capillary electrophoresis device is required to have a low sliding resistance under which a piston slides smoothly in the syringe. In addition, since the syringe is a consumable, it is also required to reduce the manufacturing cost.

Plastic syringes are widely used because the syringes can be mass-produced at a low cost. However, since these syringes are intended to be used for injection at medical sites, their pressure resistance performance is at most about ±1 atm (±0.1 MPa) (herein, −1 atm means vacuum). The plastic syringes have no pressure resistance performance against a higher pressure (>0.1 MPa) over this pressure. In other words, if the higher pressure is applied, the contents leak from the gap between the inner wall of the syringe and the piston. On the other hand, a gas-tight syringe made of glass such as a Hamilton syringe has high pressure resistance performance, but is expensive. In addition, the durability of the gas-tight syringe is low because the piston deteriorates quickly with use.

In an injector (syringe) described in Patent Document 1, the plunger pressed by a finger or the like and a portion corresponding to the piston are integrally molded, and the two are not attached or detached while being used. Therefore, the plunger and the piston are made of a rigid resin such as polypropylene. For this reason, such a piston has a small amount of deformation in the radially outside direction of the syringe when a high pressure is applied inside the syringe, and does not have high pressure resistance performance. In addition, there is a problem that the pressure resistance performance is not stable due to manufacturing variations of the piston and the syringe. Therefore, in order to obtain a high pressure resistance performance, it is necessary to precisely manufacture the shape of the piston tip in accordance with the inner diameter and surface condition of the syringe. However, it is extremely difficult to produce such a precise shape uniformly and inexpensively. Further, since the piston tip is crushed and pushed into the syringe, the sliding resistance of the piston tends to increase. As described above, the experiments by the inventors have revealed that the piston of Patent Document 1 does not necessarily have high sealing performance and stability against pressure and has high sliding resistance.

On the other hand, experiments by the inventors have revealed that the injector (syringe) described in Patent Document 2 does not always have high sealing performance against pressure and stability. Further, it has become clear from the experiments by the inventors that the injector described in Patent Document 2 shows that if the pressure is large, the outer peripheral portion of the seal portion deformed in the axial direction of the syringe is drawn into the gap between the plunger portion and the syringe. For this reason, it has become clear that a leak is likely to occur.

The invention has been made in view of such a background, and an object of the invention is to provide a piston and a syringe having a high pressure resistance performance, a good sliding performance, and an inexpensive manufacturing cost.

Solution to Problem

In order to solve the above-described problem, the present invention provides a piston which divides a space inside a cylinder into two parts, and slides inside the cylinder to pressurize or depressurize a medium made of liquid or gas stored in one space of the two parts. The piston includes a soft portion, and a rigid portion having rigidity higher than rigidity of the soft portion. The soft portion and the rigid portion are connected in series in a central axis direction of the cylinder such that the soft portion is in contact with the medium, and the rigid portion is not in contact with the medium. The soft portion does not cover an outer surface of the rigid portion at least when not in the pressurized state. The soft portion has a hollow on a surface in contact with the medium. At least at an outer peripheral portion and an end surface facing the soft portion of the rigid portion is in contact with the soft portion. A maximum outer diameter which is the maximum outer diameter of the soft portion is larger than an outer diameter of the rigid portion. An outer diameter of the rigid portion at a contact portion with the soft portion is approximately the same as an outer diameter of the soft portion at a contact portion with the rigid portion. Or, the outer diameter of the rigid portion at a contact portion with the soft portion is smaller than the outer diameter of the soft portion at the contact portion with the rigid portion, so that the entire outer peripheral portion of the soft portion does not to bend toward the rigid portion and the entire outer peripheral portion of the soft portion can be supported by the rigid portion when the soft portion moves toward the medium. The maximum outer diameter of the soft portion is larger than the outer diameter of the rigid portion to the extent that the soft portion can be supported by the rigid portion when the soft portion moves toward the medium.

Other solutions will be described in the embodiments as appropriate.

Advantageous Effects of Invention

According to the present invention, a piston and a syringe having high pressure resistance performance and good sliding performance can be provided at a low cost.

BRIEF DESCRIPTION OF DRAWINGS

FIG. 9A is a diagram (perspective view) illustrating a piston 1A of Comparative Example A.

FIG. 9B is a diagram (cross-sectional view) illustrating the piston 1A of Comparative Example A.

FIG. 11A is a diagram illustrating a relation between push distance by the piston 1A of Comparative Example A and pressure.

FIG. 11B is a diagram illustrating a relation between calculated pressure by thrust of the piston 1A of Comparative Example A and measured pressure by a sensor.

FIG. 12B is a diagram illustrating a relation between calculated pressure by thrust of the piston 1 according to this embodiment and measured pressure by a sensor.

FIG. 14A is a diagram (part 1 before pressurization) illustrating a cross-sectional view of a piston 1B of Comparative Example B.

FIG. 14B is a diagram (part 1 during pressurization) illustrating a cross-sectional view of the piston 1B of Comparative Example B.

FIG. 15A is a diagram (part 1 before pressurization) illustrating a cross-sectional view of a piston 1C of Comparative Example C.

FIG. 15B is a diagram (part 1 during pressurization) illustrating a cross-sectional view of the piston 1C of Comparative Example C.

FIG. 17A is a diagram illustrating a cross-sectional view (part 2 before pressurization) of the piston 1B of Comparative Example B.

FIG. 17B is a diagram illustrating a cross-sectional view (part 2 during pressurization) of the piston 1B of Comparative Example B.

FIG. 18A is a diagram (part 2 before pressurization) illustrating a cross-sectional view of the piston 1C of Comparative Example C.

FIG. 18B is a diagram (part 2 during pressurization) illustrating a cross-sectional view of the piston 1C of Comparative Example C.

FIG. 19 is a diagram illustrating a cross-sectional view (part 3 before pressurization) of the piston 1 of this embodiment.

FIG. 20 is a diagram illustrating a cross-sectional view (part 3 before pressurization) of the piston 1B of Comparative Example B.

FIG. 21 is a diagram illustrating a cross-sectional view (part 3 before pressurization) of the piston 1C of Comparative Example C.

FIG. 22A is a diagram (part 1) illustrating modifications of the piston 1 according to this embodiment.

FIG. 27 is a diagram schematically illustrating a cross section of another microchip 901a.

DESCRIPTION OF EMBODIMENTS

Next, modes for carrying out the present invention (referred to as "embodiments") will be described in detail with reference to the drawings as appropriate.

[Capillary Electrophoresis Device W]

Figure 1:
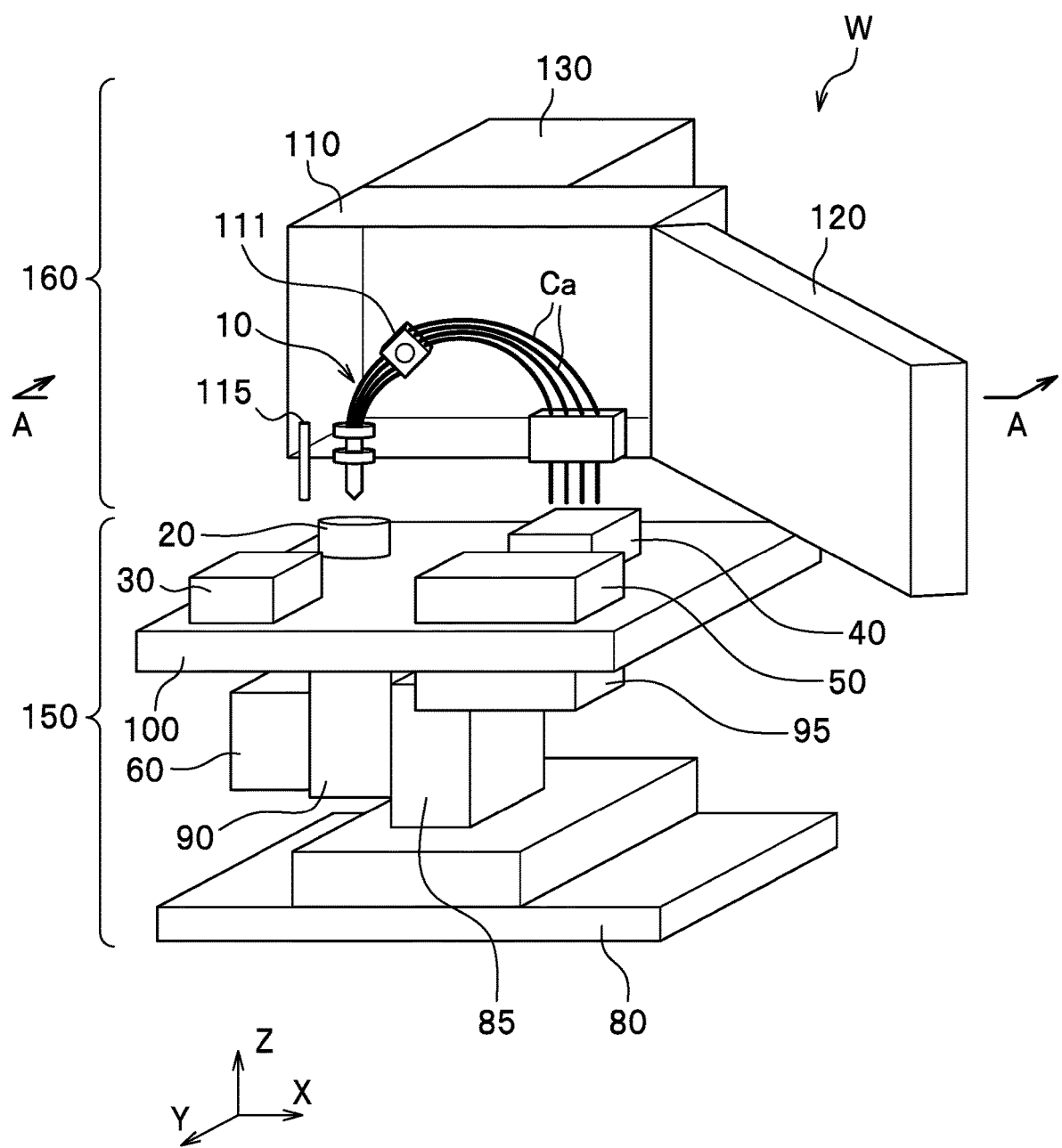
FIG. 1 is a diagram illustrating a configuration of a capillary electrophoresis device (analyzer) W according to an embodiment.

FIG. 1 is a diagram illustrating a configuration of a capillary electrophoresis device (analyzer) W according to this embodiment.

The capillary electrophoresis device W can be broadly divided into two units: an autosampler unit 150 installed at a lower part; and an irradiation detection/thermostatic chamber unit 160 installed at an upper portion.

The autosampler unit 150 is provided with a Y-axis driver 85 on a sampler base 80. The Y-axis driver 85 drives a sample tray 100 in the Y-axis direction. In addition, the Y-axis driver 85 is provided with a Z-axis driver 90. The Z-axis driver 90 drives the sample tray 100 in the Z-axis direction. On the sample tray 100, a syringe 20, an anode buffering liquid container 30, a cathode buffering liquid container 40, and a sample container 50 are set. The sample container 50 is set on an X-axis driver 95 installed under the sample tray 100. The Z-axis driver 90 is also provided with a liquid feeding mechanism 60. The liquid feeding mechanism 60 is disposed below the syringe 20.

The irradiation detection/thermostatic chamber unit 160 includes a thermostatic chamber unit 110 and a thermostatic chamber door 120. When the thermostatic chamber door 120 is closed, the inside of the thermostatic chamber unit 110 can be maintained at a constant temperature. An irradiation detection unit 130 is mounted behind the thermostatic chamber unit 110, and can perform detection during electrophoresis. The user sets a capillary array 10 in the thermostatic chamber unit 110, and the electrophoresis is performed in the thermostatic chamber unit 110 while keeping the capillary array 10 at a constant temperature. Thereafter, detection is performed by the irradiation detection unit 130. The capillary array 10 is configured by a plurality of (four in the example of FIG. 1) capillaries Ca.

The irradiation detection unit 130 irradiates each capillary Ca at a measured part 111 with a laser beam emitted from a laser emitting device (not illustrated) provided in the irradiation detection unit 130. Then, the irradiation detection unit 130 captures images of emission from each capillary Ca by an imaging device (not illustrated) provided in the irradiation detection unit 130.

Figure 2:
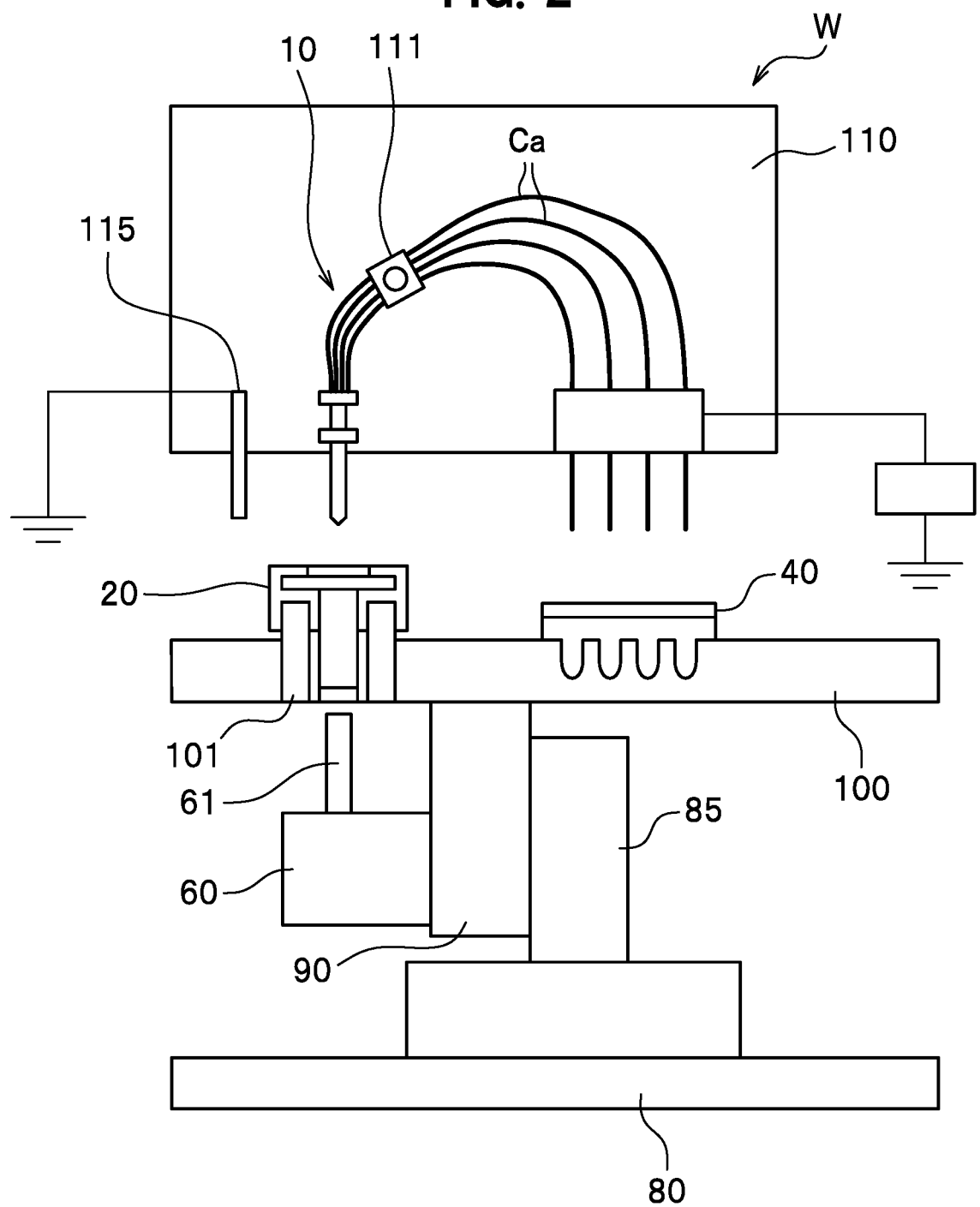
FIG. 2 is a cross-sectional view taken along line A-A in FIG. 1.

FIG. 2 is a cross-sectional view taken along line A-A in FIG. 1. In FIG. 2, the same components as those in FIG. 1 are denoted by the same symbols, and description thereof will be omitted.

The syringe 20 is inserted and set into a guide 101 embedded in the sample tray 100. In addition, the liquid feeding mechanism is arranged such that a plunger 61 provided in the liquid feeding mechanism 60 is below the syringe 20.

At the time of electrophoresis, a high voltage is applied across the cathode sides of the capillary array 10 via the cathode side buffer liquid in the cathode side buffer liquid container 40 and the anode sides of the capillary array 10 via the anode side buffer liquid in the anode side buffer liquid container 30. Here, the anode side buffer liquid is grounded through the electrode 115.

[Liquid Feeding Procedure]

Next, a procedure for filling the capillary Ca with an electrophoresis medium by the syringe 20 will be described with reference to FIGS. 3 to 5.

First, a detailed view of the syringe 20 is illustrated with reference to FIG. 3. In the syringe 20, a concave piston 1A is built in an outer cylinder 202, and sealed with a rubber stopper 203 and a cap 204 from above. Here, the piston 1A is not a piston of this embodiment but a generally-used piston. The material of the outer cylinder 202 is desirably COP, PP resin or the like, which is a resin that can be molded into a thin wall. The material of the rubber stopper 203 is desirably silicon rubber or the like which is stable for analysis. The material of the cap 204 is desirably PC, PP resin, or the like. A highly viscous liquid electrophoresis medium (medium) Q is enclosed in the syringe 20, and the air entering the syringe 20 at the time of the enclosure is made to accumulate in the upper portion. The electrophoresis medium Q is filled with a volume capable of performing analysis for 10 times. By applying a thrust to the piston 1A from the outside via the plunger 61, the piston 1A can move inside the outer cylinder 202. In other words, the piston 1A is pushed inside the outer cylinder 202.

First, the syringe 20 is set on the guide 101 for suppressing its own expansion. This guide 101 has a high rigidity. Therefore, pressure of the liquid (the electrophoresis medium Q) in the syringe 20 increases due to the pushing of the piston 1A by the plunger 61. Even if the syringe 20 expands, the expansion is suppressed at the guide 101. Further, the shape of the guide 101 is different from that illustrated in FIG. 2.

The plurality of capillaries Ca are bundled into one, inserted from the upper end side of a capillary head 201, and hermetically mounted in the capillary head 201. The lower end side of the capillary head 201 has a needle-like tip, and as illustrated in FIG. 4, the tip of the capillary head 201 pierces the rubber stopper 203, and thus the syringe 20 and the plurality of capillaries Ca are connected together. Herein, a hole through which the capillary head 201 can pass through is provided in the upper end portion of the cap 204 in advance. In addition, as illustrated in FIG. 4, the capillary head 201 is pressed against the rubber stopper 203 so that the capillary head 201 suppresses the expansion of the rubber stopper 203 due to the liquid feeding pressure.

Figure 5:
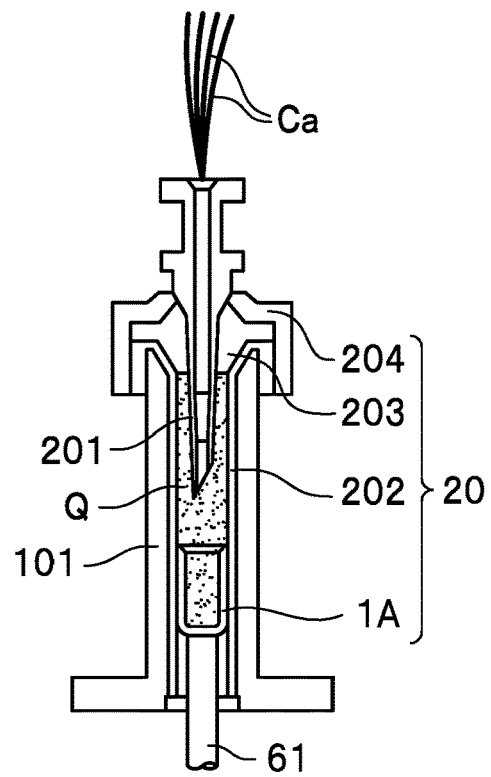
FIG. 5 is a diagram (part 3) for describing the liquid feeding procedure using the syringe 20.

As illustrated in FIG. 5, the plunger 61 pushes up the piston 1A to increase the pressure of the electrophoresis medium Q inside the syringe 20, and feeds the electrophoresis medium Q into the capillaries Ca, thereby filling the capillaries Ca with the electrophoresis medium Q.

Figure 4:
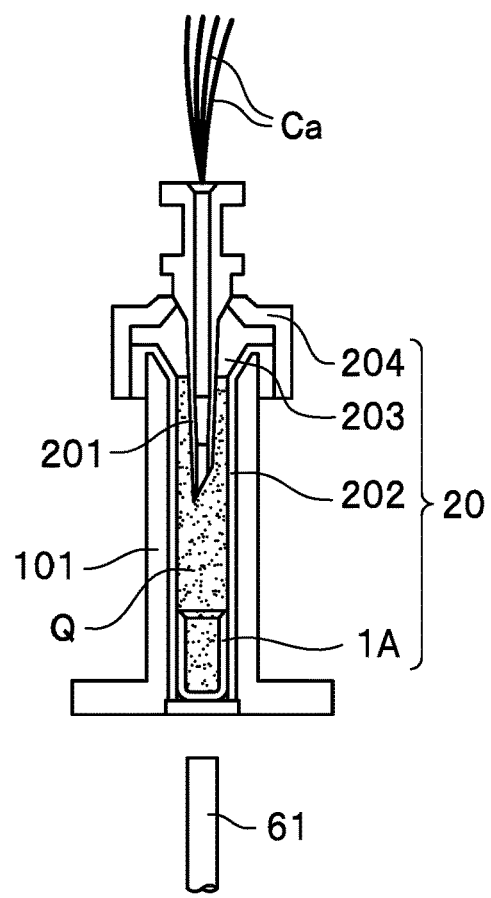
FIG. 4 is a diagram (part 2) for describing the liquid feeding procedure using the syringe 20.

When the feeding of the predetermined amount of the electrophoresis medium Q is completed, the plunger 61 is returned to the original position as illustrated in FIG. 4. Then, the piston 1A also returns to substantially the original position by the pressure inside the syringe 20. Along with this, the pressure inside the syringe 20 returns to the atmospheric pressure. However, since the volume of the electrophoresis medium Q inside the syringe is reduced by the volume filled in the capillaries Ca, the position where the piston 1A returns is slightly higher than the original position.

Since an inner diameter of each capillary Ca is very small and the electrophoresis medium Q is highly viscous, the induced pressure inside the syringe 20 due to the pushing of the plunger 61 is very high, specifically, at least 0.1 MPa or more, desirably 1 MPa or more, furthermore desirably, 5 MPa or more. For this reason, the syringe 20 is required to prevent the occurrence of leaks and have high pressure resistance.

[Piston 1]

Figure 6:
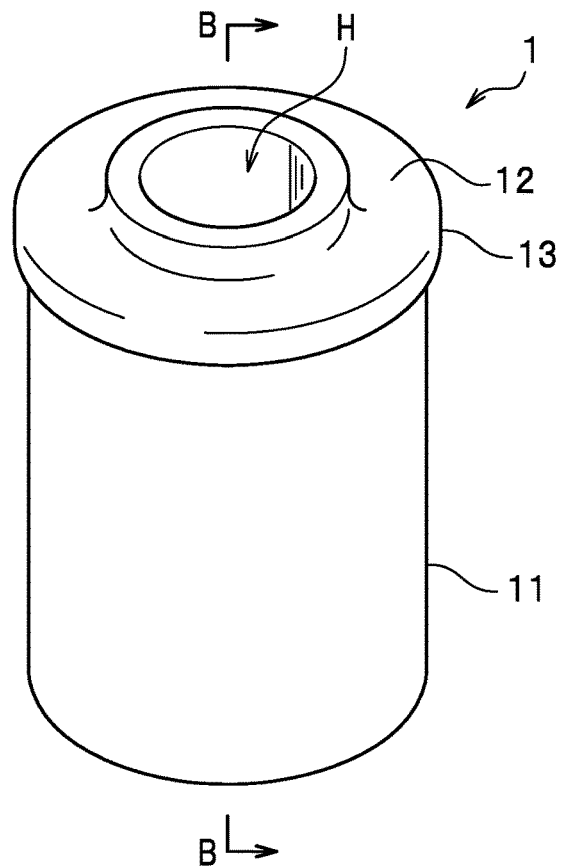
FIG. 6 is a diagram (perspective view) illustrating a configuration of a piston 1 according to this embodiment.
Figure 7:
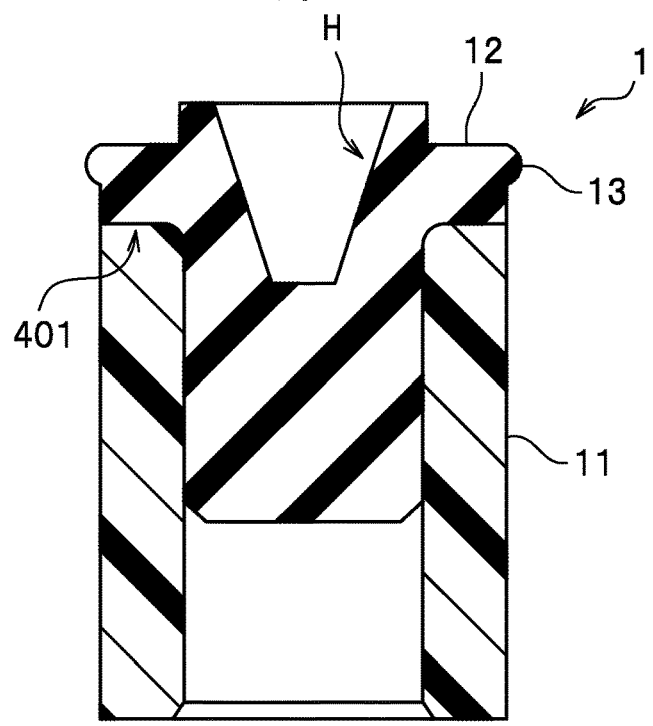
FIG. 7 is a diagram (cross-sectional view) illustrating a configuration of the piston 1 according to this embodiment.

FIGS. 6 and 7 are diagrams illustrating the configuration of a piston 1 according to this embodiment. FIG. 6 illustrates a perspective view of the piston 1, and FIG. 7 illustrates a cross-sectional view taken along line B-B of FIG. 6.

In this embodiment and the piston 1, a soft portion 12 made of highly elastic silicon rubber or the like and a rigid portion 11 made of low elastic polyethylene or the like are connected in series. The rigid portion 11 has a cylindrical shape.

The soft portion 12 is disposed on the capillary Ca side, and the rigid portion 11 is disposed on the plunger 61 side. In other words, the soft portion 12 is in contact with the electrophoresis medium Q, the rigid portion 11 is not in contact with the electrophoresis medium Q, and the soft portion 12 and the rigid portion 11 are connected in series in the axial direction of the center of the outer cylinder 202 (see FIGS. 8A and 8B).

A hollow H is provided on the capillary Ca side of the soft portion 12. The soft portion 12 has a convex portion 13 provided in the outer peripheral direction integrally with the main body of the soft portion 12. The diameter of the convex portion 13 is formed slightly larger than that of the outer periphery of the rigid portion 11. In addition, the upper surface (upper end portion) of the rigid portion 11 is in contact with a part of the soft portion 12 (at a contact portion 401). In other words, the rigid portion 11 is in contact with the soft portion 12 at least in the outer peripheral portion of the end surface facing the soft portion 12.

This contact does not need to be always kept, but needs to be kept when at least the inside of the syringe 20 (see FIGS. 8A and 8B) is pressurized. In addition, this portion may be bonded with an adhesive or the like. In FIGS. 6 and 7, the outer diameter of the soft portion 12 is larger than the outer diameter of the rigid portion 11 by the convex portion 13. However, the outer diameter of the soft portion 12 may be larger than the outer diameter of the rigid portion 11 without providing the convex portion 13. In addition, the outer diameter of the soft portion 12 when not inserted into the syringe 20 is set to be larger than the inner diameter of the syringe 20. Then the soft portion 12 is inserted into the syringe 20 while being slightly crushed. As a result, the sealing performance can be ensured even under the atmospheric pressure.

The hollow H of a truncated cone-shaped is formed on the top of the soft portion 12 (on the side of the capillary Ca).

Since the soft portion 12 is made of silicon rubber or the like, injection molding thereof is possible. In addition, since the rigid portion 11 has a simple cylindrical shape, injection molding thereof is also possible. In other words, the manufacturing cost of the piston 1 is reduced.

Figure 8A:
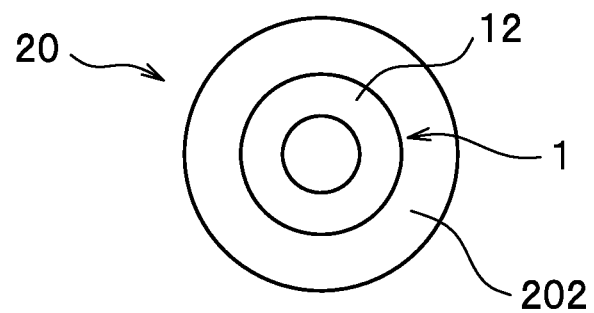
FIG. 8A is a schematic top view of the piston 1 according to this embodiment.
Figure 8B:
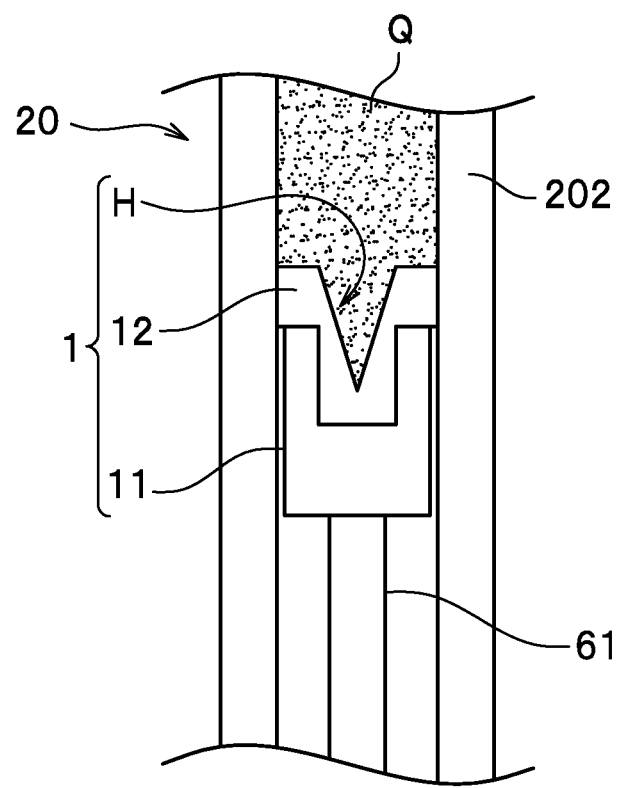
FIG. 8B is a schematic cross-sectional view of the piston 1 according to this embodiment.

FIG. 8A is a schematic top view of the piston 1 inserted in the outer cylinder 202 according to this embodiment, and FIG. 8B is a schematic cross-sectional view of the piston 1 inserted in the outer cylinder 202 according to this embodiment.

In FIGS. 8A and 8B, the outer diameter of the soft portion 12 is configured to be larger than the outer diameter of the rigid portion 11 without providing the convex portion 13 in FIGS. 6 and 7.

As illustrated in FIG. 8A, the outer periphery of the soft portion 12 is configured to be in contact with the inner wall of the outer cylinder 202 of the syringe 20.

In this way, the piston 1 divides the space inside the outer cylinder 202 into two parts, and slides inside the outer cylinder 202, so that the liquid (or gas), that is, the electrophoresis medium Q stored in one space of the two parts is pressurized or depressurized.

Next, the operation of the piston 1 will be described with reference to FIG. 8B.

When the piston 1 is pushed up by the plunger 61, the pressure of the electrophoresis medium Q inside the outer cylinder 202 increases. As a result, the electrophoresis medium Q inside the hollow H of the piston 1 generates a force that pushes out the peripheral portion of the hollow H. However, since the rigid portion 11 is located under the soft portion 12, the soft portion 12 cannot be deformed downward. Therefore, the soft portion 12 is deformed so as to be pushed in a radially outside direction. This deformation increases the force with which the soft portion 12 contacts the inner wall of the outer cylinder 202, and improves the sealing performance between the soft portion 12 and the outer cylinder 202.

Meanwhile, when the plunger 61 moves down and leaves the piston 1, the soft portion 12 quickly returns to its original shape due to elasticity thereof. Since the amount of deformation of the soft portion 12 due to the pressure applied to the electrophoresis medium Q is large, a sliding resistance is low.

As illustrated in FIG. 7, at least the vicinity of the outer periphery of the rigid portion 11 and the end surface of the rigid portion 11 facing the soft portion 12 is in contact with the soft portion 12. Then, it is desirable that the outer diameter of the soft portion 12 before being inserted into the outer cylinder 202 is larger than the inner diameter of the outer cylinder 202 as described above. In addition, the outer diameter of the rigid portion 11 is equal to or slightly smaller than the inner diameter of the outer cylinder 202. In other words, the outer diameter of the rigid portion 11 and the inner diameter of the outer cylinder 202 are close to each other. Herein, the difference between the outer diameter of the rigid portion 11 and the inner diameter of the outer cylinder 202 is small enough such that, when a high pressure is applied to the electrophoresis medium Q (when the piston 1 is pushed up), (a part of) the soft portion 12 is not drawn into the gap between the inner wall of the outer cylinder 202 and the rigid portion 11. Specifically, it has been clarified by experiments that the difference between the outer diameter of the rigid portion 11 and the inner diameter of the outer cylinder 202 needs to be 10% or less of the inner diameter of the outer cylinder 202. In other words, when the inner diameter of the outer cylinder 202 is M, the outer diameter m of the rigid portion 11 may be 0.9*M≤m≤M.

Comparative Example A

FIGS. 9A and 9B are diagrams illustrating the piston 1A of Comparative Example A. The piston 1A has a configuration and features similar to those of the piston of Patent Document 1. FIG. 9A illustrates a perspective view of the piston 1A of Comparative Example A, and FIG. 9B illustrates a cross section taken along line C-C of FIG. 9A.

The piston 1A of Comparative Example A has a bottomed cylindrical shape and is a one-piece piston made of a polyethylene resin or the like. The outer diameter of the upper end portion of the piston 1A is made to be larger than the inner diameter of the outer cylinder 202. Then, the upper end portion of the piston 1A is crushed, and thereby the piston 1A is pushed into the inside of the outer cylinder 202. As a result, the sealing performance between the piston 1A and the inner wall of the outer cylinder 202 is generated. However, the piston 1A is made of a rigid material. Therefore, it is important to make the upper end portion of the piston 1A thinner so as to be easily deformed, and to form a structure such as a contact portion of the piston 1A with the inner wall of the outer cylinder 202 precisely in accordance with the inner diameter of the outer cylinder 202. However, the piston 1A having such a structure is difficult to manufacture by injection molding. For example, since the piston 1A is made of a rigid material, if a small irregularity or a scratch is formed on the surface of the seal portion (the upper end portion of the piston 1A) during injection molding, a leak from the portion occurs. In other words, when the piston 1A is manufactured by injection molding, leakage often occurs in use, particularly when the pressure inside the syringe 20 becomes high. Therefore, the piston 1A is manufactured by manual cutting. For this reason, the manufacturing cost is high, and a precise shape of a portion of the piston 1A that contacts with the outer cylinder 202 of the syringe 20 cannot be stably manufactured, and the quality thereof is not stable. In other words, the mass productivity is low. On the contrary, as illustrated in FIG. 7, since the rigid portion 11 of the piston 1 of this embodiment has a simple cylindrical shape (there is no thin portion like the piston 1A), the manufacturing thereof can be made easily by injection molding. Further, since the piston 1A is made of a rigid material, and the piston 1A is crushed and inserted into the outer cylinder 202, the sliding resistance of the piston 1A is high. Therefore, a large force is required when the plunger 61 (see FIG. 2 and the like) pushes up the piston 1A. Consequently, only a part of the pushing force of the plunger 61 is transmitted to the inside of the syringe 20, and thus the efficiency thereof is low, and the pressure transmitted to the inside of the syringe 20 becomes unstable. In addition, even after the plunger 61 is separated from the piston 1A after the liquid feeding, the piston 1A does not move to the plunger 61 side until the pressure inside the syringe 20 returns to the atmospheric pressure. As a result, the residual pressure (a pressure higher than the atmospheric pressure) is left inside the syringe 20.

Figure 10A:
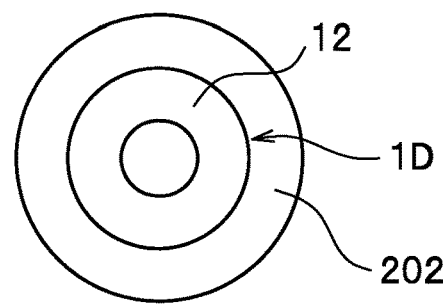
FIG. 10A is a schematic top view of the piston 1D of Comparative Example D.
Figure 10B:
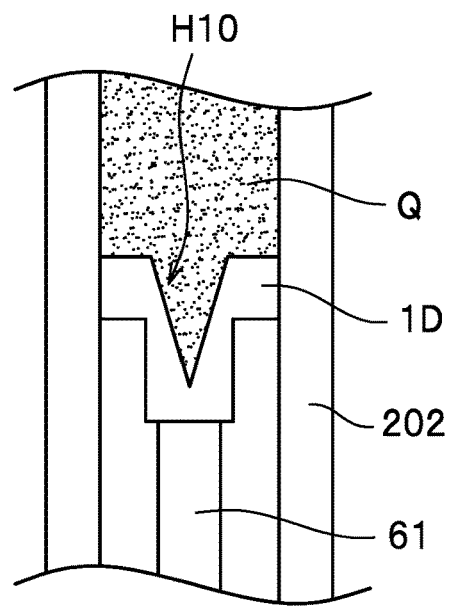
FIG. 10B is a schematic cross-sectional view of the piston 1D of Comparative Example D.

Differently from FIGS. 9A and 9B, FIG. 10A is a schematic top view of a piston 1D inserted in the outer cylinder 202 of Comparative Example D, and FIG. 10B is a schematic cross-sectional view of the piston 1D inserted in the outer cylinder 202 of Comparative Example D. The piston 1D has a configuration and features similar to those of a piston 1B of Patent Document 2 (FIGS. 14A, 14B, 17A, 17B, and 20). Unlike the piston 1A, the piston 1D is made of a soft material such as rubber. Then, the piston 1D is provided with a hollow H10 on the electrophoresis medium Q side.

Figure 10C:
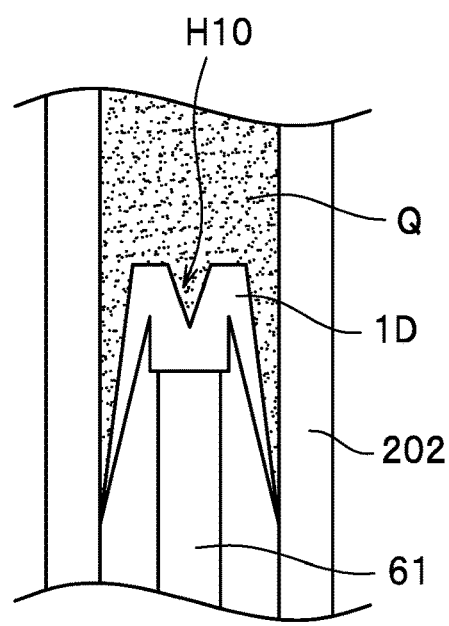
FIG. 10C is a diagram illustrating deformation of the piston 1D when the piston is pushed by a plunger 61.

In addition, FIG. 10C is a diagram illustrating deformation of the piston 1D when pushed by the plunger 61. In FIGS. 10A to 10C, the piston 1D is schematically illustrated to help with understanding, and the deformation is exaggerated in FIG. 10C.

The outer peripheral portion of the upper end of the piston 1D is in contact with the inner wall of the outer cylinder 202 of the syringe 20.

When the piston 1D is pushed up by the plunger 61, the pressure of the electrophoresis medium Q inside the syringe 20 is increased. Then, similar to the piston 1 illustrated in FIGS. 8A and 8B, the outer peripheral portion of the upper end of the piston 1D is expanded by the electrophoresis medium Q in the hollow at the center of the piston 1D. However, unlike the piston 1 illustrated in FIGS. 8A and 8B, the outer peripheral portion is not supported by the rigid portion 11. Accordingly, the outer peripheral portion of the piston 1D is pushed in the downward direction of the central axis of the outer cylinder 202 by the electrophoresis medium Q under high pressure. As a result, as illustrated in FIG. 10C, the contact portion of the piston 1D with the outer cylinder 202 is drawn between the inner wall of the outer cylinder 202 and the piston 1D and the plunger 61. As a result, the sliding resistance is further increased, the sealing performance is reduced, and when the pressure in the syringe 20 becomes high, the leakage of the electrophoresis medium Q occurs.

FIG. 11A is a diagram illustrating a relation between push distance of the piston 1A (Comparative Example A) illustrated in FIGS. 9A and 9B and induced pressure.

As illustrated in FIG. 11A, the relation between push distance and pressure show hysteresis. Herein, Step 301 in FIG. 11A illustrates a state from when the plunger 61 moves upward to when the plunger 61 starts to push up the bottom surface of the piston 1A on the way from FIG. 4 to FIG. 5. Step 302 is a state where the plunger 61 is pushing up the piston 1A. After the push-up of the piston 1A by the plunger 61 is completed, the position of the plunger 61 is fixed for about 40 seconds. Step 303 is a state from when the plunger 61 is fixed to when the plunger 61 starts to descend. The following Step 304 is a state in which the plunger 61 is descending, and the piston 1A is also descending accordingly. Further, when the push distance reaches 0 mm, the descending of the piston 1A stops, and the plunger 61 separates from the piston 1A and continues descending.

In FIG. 11A, the solid line indicates calculated pressure applied to the electrophoresis medium Q inside the syringe 20. The calculated pressure is obtained by dividing the thrust of the plunger 61 pushing the piston 1A by the inner cross-sectional area of the outer cylinder 202. On the other hand, the broken line indicates measured pressure applied to the electrophoresis medium Q inside the syringe 20. The measured pressure was directly obtained by the pressure sensor. The solid and dashed lines preferably coincide with each other, but as shown in FIG. 11A, the solid line and the broken line are separated. This deviation indicates a pressure loss due to sliding resistance.

Specifically, after 30 seconds from the completion of the pushing operation by the plunger 61, the calculated pressure indicated by the solid line is 9.6 MPa, whereas the measured pressure indicated by the broken line is 7.3 MPa. Therefore, the difference therebetween indicated by Symbol D1 of 9.6−7.3=2.3 MPa is the pressure loss. Ratio of the pressure loss is 2.3/7.3≈0.315, that is, a pressure loss of 32% pressure loss has occurred. Note that such a large pressure loss is due to a high sliding resistance. In other words, even if the piston 1A is pushed in with 100% force, 32% of the force is lost to the sliding resistance, and only the remaining 68% of the force is transmitted to the internal electrophoresis medium Q. In addition, since the sliding resistance varies due to manufacturing variations of the piston 1A, there is a problem that the pressure applied to the internal electrophoresis medium Q becomes unstable.

In addition, when the push distance returns to 0 mm, the calculated pressure indicated by the solid line becomes 0 MPa, whereas the measured pressure indicated by the broken line becomes 0.35 MPa (Symbol D2). In other words, even if the plunger 61 is separated from the piston 1A, because the sliding resistance of the piston 1A is large, the piston 1A cannot completely return to the position before the pushing, and a pressure of 0.35 MPa of the electrophoresis medium Q inside the syringe 20 still remains. If such a residual pressure is present, when the capillary head 201 is inserted into the syringe 20 through the rubber stopper 203 on the way from FIG. 3 to FIG. 4, the electrophoresis medium Q inside the syringe 20 leaks out of the gap, and the surroundings may be contaminated. In addition, when the sliding resistance is large as described above, the following problem also occurs. In other words, while returning from the state of FIG. 4 to the state of FIG. 3, the capillary head 201 is pulled out of the syringe 20 through the rubber stopper 203. At this time, the electrophoresis medium Q inside the syringe 20 has a negative pressure (a pressure lower than the atmospheric pressure and close to a vacuum), which may cause generation of air bubbles and adversely affect the analysis.

In addition, as described above, since the piston 1A according to Comparative Example A is manufactured by cutting, there is a problem that the manufacturing cost is high and the quality is not stable. Further, since the piston 1A according to Comparative Example A has a high sliding resistance, application of pressure inside the syringe 20 is inefficient and unstable. Moreover, there is also a problem that the residual pressure is high when the plunger 61 is separated from the piston 1A and the plunger 61 is not pushing the piston 1A.

FIG. 11B illustrates the data of FIG. 11A in a different expression. The horizontal axis represents calculated pressure (obtained by dividing thrust by the inner cross-sectional area of the outer cylinder 202), and the vertical axis represents measured pressure directly obtained by the pressure sensor.

It is desirable that calculated pressure and measured pressure match with each other. In other words, the relation between calculated pressure and measured pressure is desirably a straight line having a slope 1 passing through the origin as illustrated by a broken line in FIG. 11B. However, as illustrated in FIG. 11B, the relation between calculated pressure and measured pressure largely deviates from the straight line indicated by the broken line, and shows a large hysteresis.

Figure 12A:
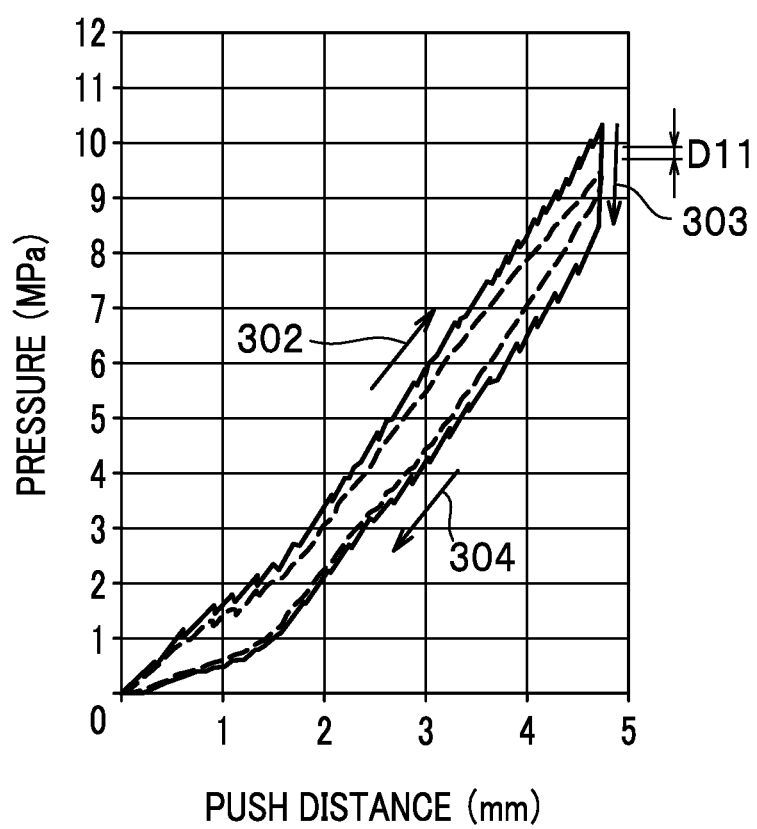
FIG. 12A is a diagram illustrating a relation between push distance by the piston 1 and pressure according to this embodiment.

FIGS. 12A and 12B are diagrams illustrating the results of experiments using the piston 1 (the piston 1 illustrated in FIGS. 6 and 7) according to this embodiment.

FIG. 12A is a diagram illustrating a relation between push distance of the piston 1 and induced pressure according to this embodiment.

In FIG. 12A, the solid and broken lines are the same as in FIG. 11A. Further, in FIG. 12A, Step 301 does not exist.

As illustrated in FIG. 12A, the solid and broken lines are closer together compared to those in FIG. 11A. Symbol D11 indicates a pressure loss. Ratio of the pressure loss is D11=0.24/9.2=0.026. In other words, the pressure loss is only 2.6%.

Further, the measured pressure indicated by the broken line is 0.0077 MPa, that is, almost zero at the point where the push distance is 0 mm in FIG. 12A. In other words, the residual pressure hardly occurs.

Consequently, both the pressure loss and the residual pressure of the piston 1 of this embodiment can be reduced by one digit or more compared to those of the piston 1A of Comparative Example A.

Further, since the soft portion 12 is made of silicon rubber or the like, the soft portion 12 can be manufactured by injection molding. Since the rigid portion 11 has a simple cylindrical shape and does not need to be formed into a precise shape, the rigid portion 11 can also be manufactured by injection-molding. As a result, the manufacturing cost of the piston 1 of this embodiment can be significantly reduced as compared with that of the piston 1A of Comparative Example A.

FIG. 12B is a graph similar to FIG. 11B.

As illustrated in FIG. 12B, with the use of the piston 1 according to this embodiment, calculated pressure and measured pressure are close to each other, and it can be seen that a relation between both pressures are close to an ideal relation (the straight line of a slope 1 passing through the origin indicated by the broken line).

[Features of Piston 1]

Hereinafter, the piston 1 illustrated in FIGS. 6 and 7, in which a soft portion 12 made of a material with high elasticity and a rigid portion 11 made of a material with low elasticity are connected in series, will be compared with the piston 1B (FIGS. 14A, 14B, 17A, 17B, and 20) and a piston 1C (FIGS. 15A, 15B, 18A, 18B, and 21) which have a similar structure. In a case where the plunger 61 and the pistons 1B or 1C are used integrally as the pistons 1B and 1C (in a case where both are not attached or detached during use), the plunger 61 is regarded as the rigid portion 11 of the piston 1. In addition, the medium contained in the syringe 20 will be mainly considered the electrophoresis medium Q including the separation medium, but may be a gas.

With reference to FIGS. 13A to 20, the characteristics of the piston 1 of this embodiment and the pistons 1B and 1C of the comparative example will be compared. Further, the piston 1B (FIGS. 14A, 14B, 17A, 17B, and 20) is a piston in Patent Document 2 (hereinafter, referred to as Comparative Example B). In addition, as described above, a piston 1D (see FIGS. 10A, 10B, and 10C) is another form of the piston 1B in Patent Document 2. On the other hand, the piston 1C (FIGS. 15A, 15B, 18A, 18B, and 21) is a piston in JP 2004-24768 A (hereinafter, referred to as Comparative Example C).

Figure 3:
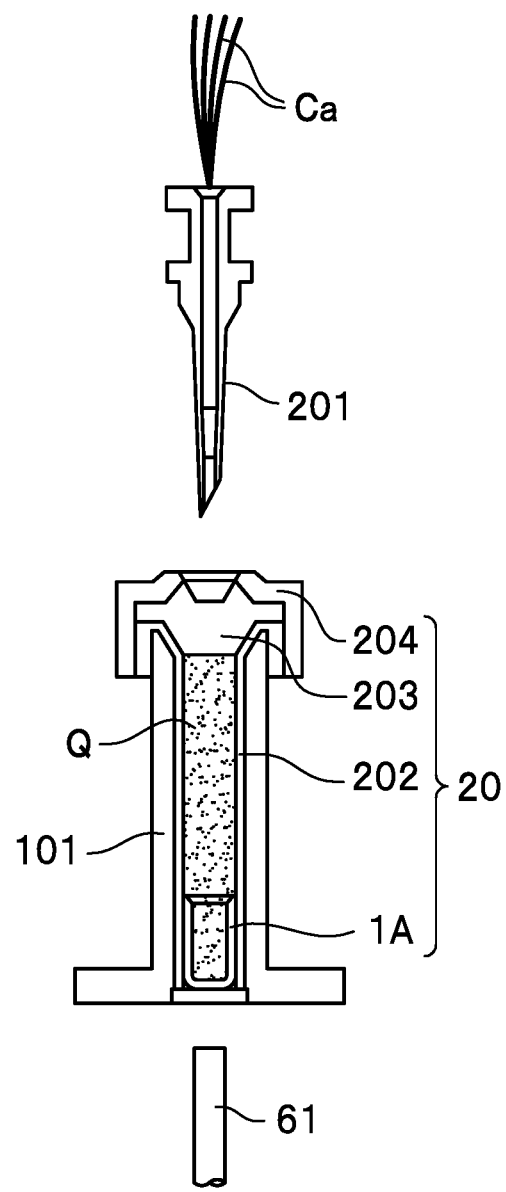
FIG. 3 is a diagram (part 1) for describing a liquid feeding procedure using a syringe 20.

FIGS. 3 to 5 will be referred to as appropriate. In FIGS. 13A to 20, the downward direction is the direction of the plunger 61, and the upward direction (the direction of arrow of the central axis T) is the direction of the electrophoresis medium Q and the direction of the capillary Ca (positive direction). In FIGS. 13A, 13B, 14A, 14B, 16A, 16B, 17A, 17B, 19, and 20, although only the pistons 1 and 1B are illustrated, they represent pistons inserted in the outer cylinder 202 of the syringe 20 containing the electrophoresis medium Q. In addition, in FIGS. 13B, 14B, 15B, 16B, 17B, and 18B, an outlined arrow indicates that the electrophoresis medium Q is in a pressurized state. The direction of the outlined arrow indicates a representative direction of the pressure, and does not indicate all directions of the pressure. Actually, pressures in the vertical directions are generated on all surfaces of the soft portion 12 in contact with the electrophoresis medium Q.

In FIGS. 13A to 20, the same components are denoted by the same symbols, and description thereof will be omitted.

Figure 13A:
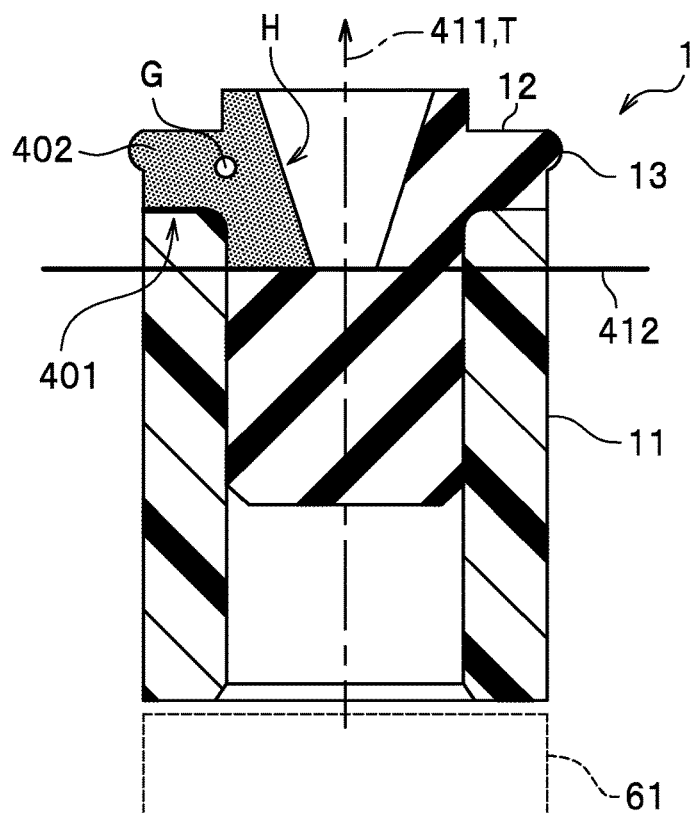
FIG. 13A is a diagram (part 1 before pressurization) illustrating a cross-sectional view of the piston 1 of this embodiment.
Figure 13B:
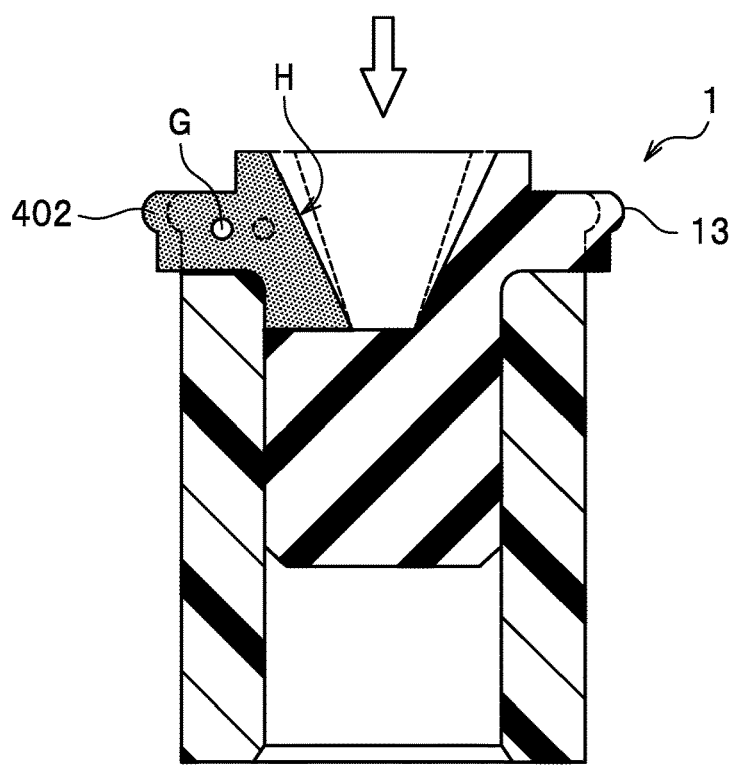
FIG. 13B is a diagram (part 1 during pressurization) illustrating a cross-sectional view of the piston 1 of this embodiment.

FIGS. 13A and 13B are cross-sectional views of the piston 1 of this embodiment. FIG. 13A illustrates an unpressurized piston 1, whereas FIG. 13B illustrates pressurized piston 1. In FIG. 13B, a broken line indicates the unpressurized piston 1 (shape before deformation).

Herein, the operation of the piston 1 according to this embodiment will be described again with reference to FIG. 13B.

As illustrated in FIG. 13B, when pressure is applied to the electrophoresis medium Q by pushing the piston 1 by the plunger 61, the peripheral portion of the hollow H of the soft portion 12 is pushed in the outer peripheral direction by the electrophoresis medium Q in the hollow H. As a result, the convex portion 13 is pressed against the inner wall of the outer cylinder 202. In FIG. 13B, the piston 1 is illustrated on an assumption that the outer cylinder 202 of the syringe 20 (see FIGS. 8A and 8B) does not exist, and the peripheral portion can be freely deformed in the outer peripheral direction. However, the peripheral portion comes in contact against the inner wall of the outer cylinder 202, so that the amount of deformation is slightly smaller. With this configuration, the sealing performance is improved, and the electrophoresis medium Q is prevented from leaking. Of course, the entirety of the soft portion 12 is also pushed to the downward direction, but as illustrated in FIG. 13A, the soft portion 12 is supported by the rigid portion 11 via the contact portion 401 with the rigid portion 11, so that the deformation of the soft portion 12 in the downward direction is suppressed.

When the liquid feeding is completed and the plunger 61 is separated from the piston 1, the pressure of the electrophoresis medium Q returns to the atmospheric pressure, and the soft portion 12 quickly returns to the original state shown in FIG. 13A. Then, the pressing of the convex portion 13 against the inner wall of the outer cylinder 202 becomes weak. As a result, the sliding resistance with the inner wall of the outer cylinder 202 is reduced, and the piston 1 quickly returns to the original position before the plunger 61 is pushed (more precisely, the piston 1 returns to a position higher than the original position according to a volume of the electrophoresis medium Q filled in the capillary Ca). As a result, the residual pressure in the syringe 20 disappears.

The characteristic of the piston 1 having a small sliding resistance and a high sealing performance is that when the pressure of the electrophoresis medium Q in the syringe 20 increases, a deformation of the portion of the piston 1 in contact with the electrophoresis medium Q in the radially outside direction of the syringe 20 occurs (a larger deformation is better) while a deformation thereof in the direction of the central axis T of the syringe 20 is reduced (a less deformation is better). The portion of the piston 1 that is in contact with the electrophoresis medium Q is made of a material having flexibility and elasticity. It is preferable that its deformation in the radially outside direction due to the above-mentioned increase in pressure is increased and, at the same time, its shape returns to the original shape when the pressure is reduced. In addition, the width of the portion of the piston 1 pressed against the inner wall of the outer cylinder 202 (see FIG. 8B) of the syringe 20, by the deformation in the radially outside direction of the piston 1, in the direction of the central axis T of the syringe 20 is desirable to be made smaller. If the width is large, the sealing performance is reduced, and the sliding resistance is increased.

First Shape Feature

This Embodiment

Next, the shape characteristics (first shape characteristics) of the piston 1 according to this embodiment will be described.

First, in the cross-sectional view of FIG. 13A, a straight line 411 is defined such that it passes through the center of the bottom surface of the hollow H (or passes through the deepest portion of the hollow H in a case where there is no bottom surface) and is parallel to the central axis T of the piston 1. As illustrated in FIG. 13A, the straight line 411 coincides with the central axis T of the piston 1.

Further, in the cross-sectional view of FIG. 13A, a straight line 412 is defined such that it passes through the center of the bottom surface of the hollow H (or passes through the deepest portion of the hollow H when there is no bottom surface) and is orthogonal to the central axis T of the piston 1.

Then, in the cross-sectional view of FIG. 13A, partial regions of the soft portion 12 are defined such that they are outside the straight line 411 (the left side or the right side of the straight line 411 in FIG. 13A) and on the electrophoresis medium Q side from the straight line 412 (above the straight line 412 in FIG. 13A). There are two such regions in the radial direction (on the left and right sides in FIG. 13A), and one of the regions is a region (first region) 402 (the left side in FIG. 13A is selected). Then, the centroid of the region 402 is defined as the centroid G. At this time, as illustrated in FIGS. 13A and 13B, the piston 1 according to this embodiment has the following features (A1) to (A4). These are derived as shape requirements for realizing the characteristics of the piston 1. Further, the centroid G is the centroid of the surface having no thickness (the cross section of the soft portion 12). The same applies to the subsequent centroid G.

In other words, if the direction from the rigid portion 11 to the soft portion 12 is set positive, the region 402 is a part of the soft portion 12 radially outward from the position of the deepest part of the hollow H and positive from the position of the deepest part, in a longitudinal section of the soft portion 12, including the deepest portion of the hollow H and the central axis T.

(A1) At least at the time of pressurization, in the region 402, there is a contact portion 401 that contacts the rigid portion 11 or the plunger 61, and at least at a part of the contact portion 401, the contact surface of the rigid portion 11 or the plunger 61 faces the electrophoresis medium Q side (the upper side in FIG. 13A), and the contact surface of the region 402 faces the plunger 61 side (the lower side in FIG. 13A).

(A2) At least a part of the contact portion 401 satisfying the above (A1) is located radially outside the centroid G (the left side of the centroid G in FIG. 13A).

(A3) At least a part of the contact portion 401 satisfying the above (A1) is located on the electrophoresis medium Q side (the upper side in FIG. 13A) of the bottom surface of the hollow H (in a case where there is no bottom surface, the deepest portion of the hollow H).

(A4) When the piston 1 is deformed by the pressurization, the movement of the centroid G in the radially outside direction (the left direction in FIG. 13B) is larger than that in the direction toward the plunger 61 (the downward direction in FIG. 13B).

Comparative Example B

FIGS. 14A and 14B are diagrams illustrating a cross-sectional view of the piston 1B of Comparative Example B. FIG. 14A illustrates the piston 1B before pressurization, and FIG. 14B illustrates the piston 1B during pressurization. The piston 1 illustrated in FIGS. 13A and 13B has the hollow H at the center of the upper surface. On the other hand, the piston 1B illustrated in FIGS. 14A and 14B has a ring-shaped groove provided concentrically with the outer periphery on the upper surface. For this reason, FIGS. 14A and 14B illustrate two hollows H1, that is, ring-shaped grooves, on both left and right sides with respect to the central axis T of the piston 1B.

In addition, in FIGS. 14A and 14B, those having the same definitions as those in FIGS. 13A and 13B are denoted by the same symbols. Herein, in FIGS. 14A and 14B, a portion where the plunger 61 is in contact with the piston 1B and a force is applied when the plunger 61 is pushed is illustrated as the contact portion 401. Further, in FIG. 14A, the broken line indicates the shape of the piston 1B before pressurization (before deformation).

When pressure is applied to the electrophoresis medium Q as illustrated in FIG. 14B, a portion of the piston 1B in Comparative Example B outside the hollow H1 on the electrophoresis medium Q side of the piston 1B is curved to the plunger 61 side (the lower side in FIG. 14B). For this reason, the force with which the curved portion is pressed against the inner wall of the outer cylinder 202 does not change much with and without pressurization. The piston 1B is made of a highly flexible material, and corresponds to the soft portion 12 of the piston 1. The plunger 61 illustrated by a dotted line in FIG. 14A also serves as the rigid portion 11 of the piston 1. In addition, the piston 1B and the plunger 61 are integrated, and are not detachable like the piston 1 and the plunger 61.

Herein, in Comparative Example B, the conditions (A1) to (A4) described above will be considered.

(A1) In the region 402, since there is no equivalent to the contact portion 401 illustrated in FIG. 13A, (A1) does not hold.

(A2) In the region 402, since there is no equivalent to the contact portion 401 illustrated in FIG. 13A, (A2) does not hold.

(A3) In the region 402, since there is no equivalent to the contact portion 401 illustrated in FIG. 13A, (A3) does not hold.

(A4) As illustrated in FIG. 14B, the moving direction of the centroid G due to the deformation caused by the pressure is more toward the plunger 61 (the downward direction in FIG. 14B) than radially outward (the left direction in FIG. 14B). Therefore, (A4) does not hold.

The reason that the region 402 of the piston 1B is deformed mainly toward the plunger 61 rather than radially outward is that the deformation of the center portion of the piston 1B toward the plunger 61 is suppressed by the plunger 61, but there is no support for suppressing the deformation of the outer peripheral portion of the piston 1B toward the plunger 61. Therefore, when a high pressure is applied to the electrophoresis medium Q, the outer peripheral portion of the soft portion 12, that is, the region 402 is excessively deformed in the direction of the plunger 61 as in the piston 1D in FIG. 10C, and the sealing performance cannot be maintained.

Comparative Example C

FIGS. 15A and 15B are diagrams illustrating a cross-sectional view of the piston 1C of Comparative Example C. FIG. 15A illustrates the piston 1C before pressurization, and FIG. 15B illustrates the piston 1C during pressurization. Similarly to the piston 1 illustrated in FIGS. 13A and 13B, the piston 1C is provided with a hollow H2 on the center of the upper surface.

In FIGS. 15A and 15B, the components having the same definitions as those in FIGS. 13A and 13B are denoted by the same symbols. Further, in FIG. 15B, a broken line indicates a shape of the piston 1C before pressurization (before deformation).

When pressure is applied to the electrophoresis medium Q as illustrated in FIG. 15B, the outer peripheral portion of the piston 1C in Comparative Example C bends (deforms) toward the plunger 61 (the lower side in FIG. 15B). Therefore, the force with which the piston 1C is pressed against the inner wall of the outer cylinder 202 does not change much with and without pressurization. The piston 1C is made of a highly flexible material. This corresponds to the soft portion 12 of the piston 1. The plunger 61 also functions as the rigid portion 11 of the piston 1. In addition, the piston 1C and the plunger 61 are integrated, and are not detachable like the piston 1 and the plunger 61.

Herein, in Comparative Example C, the conditions (A1) to (A4) described above will be considered.

(A1) In the region 402, since there is no equivalent to the contact portion 401 illustrated in FIG. 13A, (A1) does not hold.

(A2) In the region 402, since there is no equivalent to the contact portion 401 illustrated in FIG. 13A, (A2) does not hold.

(A3) In the region 402, since there is no equivalent to the contact portion 401 illustrated in FIG. 13A, (A3) does not hold.

(A4) As illustrated in FIG. 15B, the moving direction of the centroid G due to deformation caused by pressurization is more toward the plunger 61 (the downward direction in FIG. 15B) than radially outward (the left direction in FIG. 15B). Therefore, (A4) does not hold.

The reason that the region 402 of the piston 1C is deformed mainly toward the plunger 61 rather than radially outward is that the deformation of the center portion of the piston 1C toward the plunger 61 is suppressed by the plunger 61, but there is no support for suppressing the deformation of the outer peripheral portion of the piston 1C toward the plunger 61. Therefore, when a high pressure is applied to the electrophoresis medium Q, the outer peripheral portion of the soft portion 12, that is, the region 402 is excessively deformed in the direction of the plunger 61 as in the piston 1D in FIG. 10C, and the sealing performance cannot be maintained.

Second Shape Feature

Next, features (second shape features) of the piston 1 of this embodiment will be described with reference to FIGS. 16A to 18B from a different viewpoint from FIGS. 13A to 15B.

This Embodiment

Figure 16A:
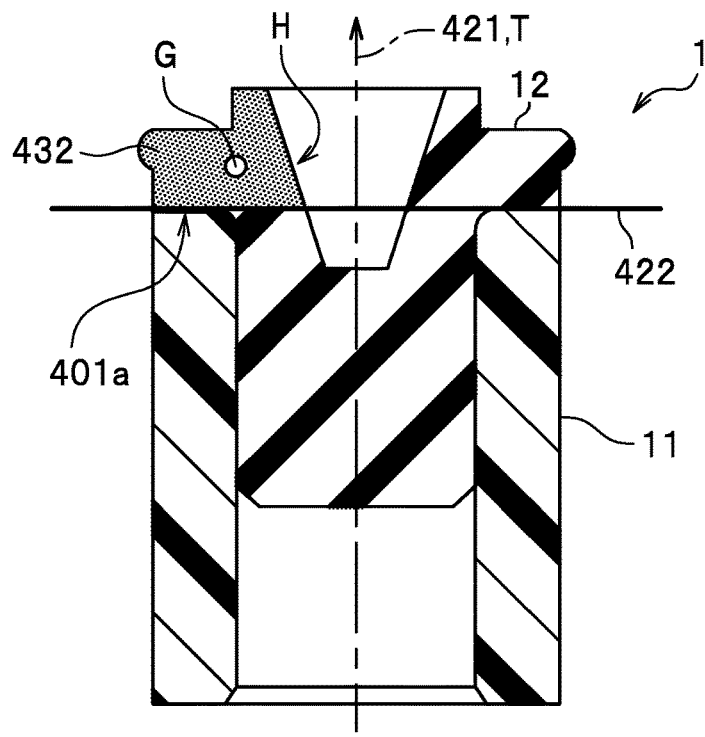
FIG. 16A is a diagram illustrating a cross-sectional view (part 2 before pressurization) of the piston 1 according to this embodiment.
Figure 16B:
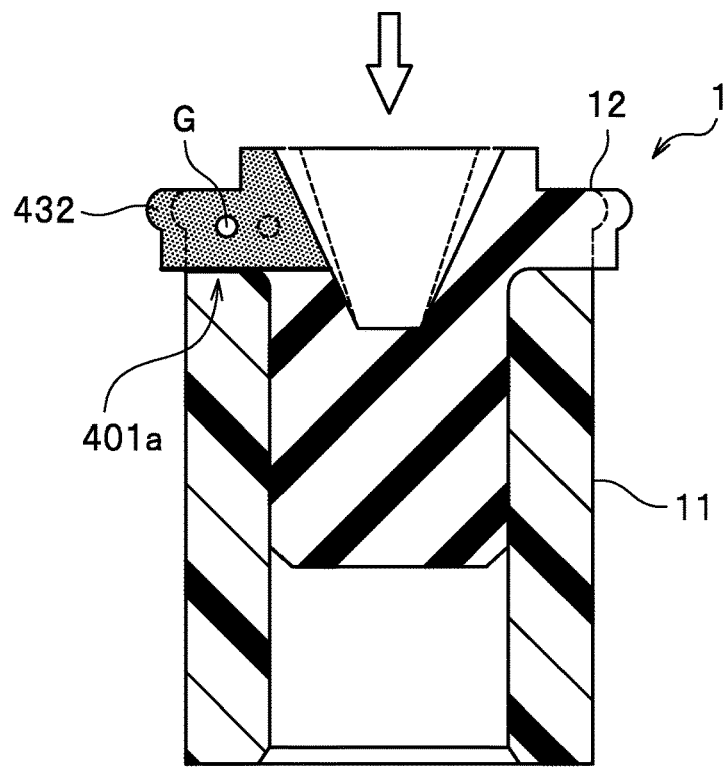
FIG. 16B is a diagram (part 2 during pressurization) illustrating a cross-sectional view of the piston 1 according to this embodiment.

FIGS. 16A and 16B are cross-sectional views of the piston 1 according to this embodiment. FIG. 16A illustrates the piston 1 before pressurization, and FIG. 16B illustrates the piston 1 during pressurization. In FIG. 16B, a broken line indicates the piston 1 before pressurization (before deformation). The piston 1 illustrated in FIGS. 16A and 16B is the same as the piston 1 illustrated in FIGS. 13A and 13B, and the definitions of the straight line 421, the straight line 422, the region 432, and the like are different from those in FIGS. 13A and 13B.

First, in the cross-sectional view of FIG. 16A, a straight line 421 is defined such that it passes through the center of the bottom surface of the hollow H (or passes through the deepest portion of the hollow H in a case where there is no bottom surface) and is parallel to the central axis T of the piston 1. As illustrated in FIG. 16A, the straight line 421 coincides with the central axis T of the piston 1.

Further, a contact portion 401a where the soft portion 12 contacts the rigid portion 11 or the plunger 61 at least at the time of pressurization and which is closest to the electrophoresis medium Q (the upper side in FIG. 16A) is defined. In addition, a straight line 422 passing through the contact portion 401a and orthogonal to the central axis T of the piston 1 is defined.

Then, in the cross-sectional view of FIG. 16A, partial regions of the soft portion 12 are defined such that they are outside the straight line 421 (the left side or the right side of the straight line 421 in FIG. 16A) and on the electrophoresis medium Q side from the straight line 422 (above the straight line 422 in FIG. 16A). There are two such regions in the radial direction (on the left and right sides in FIG. 16A), and one of the regions is a region (second region) 432 (the left side in FIG. 16A is selected). Then, the centroid of the region 432 is defined as the centroid G. At this time, as illustrated in FIGS. 16A and 16B, the piston 1 according to this embodiment has the following features (B1) to (B3). These are derived as shape requirements for realizing the characteristics of the piston 1.

In other words, if the direction from the rigid portion 11 to the soft portion 12 is set positive, the region 432 is a part of the soft portion 12 radially outward from the position of the deepest part of the hollow H and positive from the straight line 422 which is perpendicular to the central axis T and passes through the position in the most positive direction in the contact portion 401a where the rigid portion 11 and the soft portion 12 are in contact with each other, in a longitudinal section of the soft portion 12, including the deepest portion of the hollow H and the central axis T.

(B1) The region 432 includes at least a portion of the contact portion 401a on the radially outside of the centroid G (the left side in FIG. 16A), and at this portion, the contact surface of the rigid portion 11 or the plunger 61 faces the electrophoresis medium Q side (the upper side in FIG. 16A), and the contact surface of the region 432 faces the plunger 61 side (the lower side in FIG. 16A).

(B2) At least a part of the contact portion 401a satisfying the above (B1) is on the electrophoresis medium Q side (the upper side in FIG. 16A) of the bottom surface of the hollow H (or the deepest portion).

(B3) When the piston 1 is deformed by the pressurization, the movement of the centroid G in the radially outside direction (the left side direction in FIG. 16B) is larger than that in the direction toward the plunger 61 (the downward direction in FIG. 16B).

Comparative Example B

FIGS. 17A and 17B are diagrams illustrating cross-sectional views of the piston 1B of Comparative Example B. FIG. 17A illustrates the piston 1B before pressurization, and FIG. 17B illustrates the piston 1B during pressurization. The piston 1B illustrated in FIGS. 17A and 17B is the same as the piston 1B illustrated in FIGS. 14A and 14B, and the definitions of the straight line 421, the straight line 422, the region 432, and the like are different from those in FIGS. 14A and 14B.

In FIGS. 17A and 17B, the components having the same definitions as those in FIGS. 16A and 16B are denoted by the same symbols. Herein, in FIGS. 17A and 17B, a portion where the plunger 61 is in contact with the piston 1B and a force is applied when the plunger 61 is pushed is illustrated as the contact portion 401a.

Herein, in Comparative Example B, the conditions (B1) to (B3) described above will be considered.

(B1) In the region 432, since there is no equivalent to the contact portion 401a illustrated in FIG. 16A, (B1) does not hold.

(B2) In the region 432, since there is no equivalent to the contact portion 401a satisfying (B1), (B2) does not hold.

(B3) The moving direction of the centroid G due to the deformation of the piston 1B caused by the pressurization is more toward the plunger 61 (the lower side in FIG. 17B) than radially outward (the left side in FIG. 17B). Therefore, (B3) does not hold.

Comparative Example C

FIGS. 18A and 18B are diagrams illustrating a cross-sectional view of the piston 1C of Comparative Example C. FIG. 18A illustrates the piston 1C before pressurization, and FIG. 18B illustrates the piston 1C during pressurization. The piston 1C illustrated in FIGS. 18A and 18B is the same as the piston 1C illustrated in FIGS. 15A and 15B, and the definitions of the straight line 421, the straight line 422, the region 432, and the like are different from those in FIGS. 15A and 15B.

In FIGS. 18A and 18B, the components having the same definitions as those in FIGS. 16A and 16B are denoted by the same symbols.

Herein, in Comparative Example C, the conditions (B1) to (B3) described above will be considered.

(B1) On the radially outside the centroid G in the region 432 (the left side in FIG. 18A), since there is no equivalent to the contact portion 401a illustrated in FIG. 16A, (B1) does not hold.

(B2) In the region 432, since there is no equivalent to the contact portion 401a satisfying (B1), (B2) does not hold.

(B3) The moving direction of the centroid G due to the deformation of the piston 1C caused by the pressurization is more toward the plunger 61 (the lower side in FIG. 18B) than radially outward (the left side in FIG. 18B). Therefore, (B3) does not hold.

Third Shape Feature

Next, features (third shape features) of the piston 1 of this embodiment will be described with reference to FIGS. 19 to 21 from a different viewpoint from FIGS. 13A to 18B.

This Embodiment

FIG. 19 is a cross-sectional view of the piston 1 of this embodiment. FIG. 19 illustrates the piston 1 before pressurization. The piston 1 illustrated in FIG. 19 is the same as the piston 1 illustrated in FIGS. 13A, 13B, 16A, and 16B, and the definitions of the straight line 441, the region 452, and the like are different from those in FIGS. 13A and 13B. The shape of the piston 1 during pressurization is the same as in FIGS. 13B and 16B.

First, a straight line 441 that passes through the center of the bottom surface of the hollow H (or passes through the deepest portion of the hollow H in a case where there is no bottom surface) and is parallel to the central axis T of the piston 1 is defined. As illustrated in FIG. 19, the straight line 441 coincides with the central axis T of the piston 1.

Then, regions of the soft portion 12 outside the straight line 441 is defined. There are two such regions in the radial direction (on the left and right sides in FIG. 19), and one of the regions is a region (third region) 452 (the left side in FIG. 19 is selected). Then, the centroid of the region 452 is defined as the centroid G. At this time, as illustrated in FIG. 19, the piston 1 according to this embodiment has the following features (C1) and (C2). These are derived as shape requirements for realizing the characteristics of the piston 1.

In other words, the region 452 is a part of the soft portion 12 radially outward from the position of the deepest part of the hollow H, in a longitudinal section of the soft portion 12 including the deepest portion of the hollow H and the central axis T.

(C1) At least at the time of pressurization, on the radially outside from the centroid G in the region 452 (the left side in FIG. 19), there is a contact portion 401b that contacts the rigid portion 11, and at least at a part of the contact portion 401b, the contact surface of the rigid portion 11 or the plunger 61 faces the electrophoresis medium Q side (the upper side in FIG. 19), and the contact surface of the region 452 faces the plunger 61 side (the lower side in FIG. 19).

(C2) At least a part of the contact portion 401b is located on the electrophoresis medium Q side (the upper side in FIG. 19) of the bottom surface of the hollow H (or the deepest portion).

Comparative Example B

FIG. 20 is a diagram illustrating a cross-sectional view of the piston 1B of Comparative Example B. FIG. 20 illustrates the piston 1B before pressurization. The piston 1B illustrated in FIG. 20 is the same as the piston 1B illustrated in FIGS. 14A, 14B, 17A, and 17B, and the definitions of the straight line 441, the region 452, and the like are different from those in FIGS. 14A and 14B. The shape of the piston 1B during pressurization is the same as in FIGS. 14B and 17B. Herein, in FIG. 20, a portion where the plunger 61 is in contact with the piston 1B and a force is applied when the plunger 61 is pushed is illustrated as the contact portion 401b.

In addition, in FIG. 20, the components having the same definitions as those in FIG. 19 are denoted by the same symbols.

Herein, in Comparative Example B, the conditions (C1) and (C2) described above will be considered.

(C1) In the region 452, since there is no equivalent to the contact portion 401b illustrated in FIG. 19, (C1) does not hold.

(C2) In the region 452, since there is no equivalent to the contact portion 401b illustrated in FIG. 19, (C2) does not hold.

Comparative Example C

FIG. 21 is a diagram illustrating a cross-sectional view of the piston 1C of Comparative Example C. FIG. 21 illustrates the piston 1C before pressurization. The piston 1C illustrated in FIG. 21 is the same as the piston 1C illustrated in FIGS. 15A, 15B, 18A, and 18B, and the definitions of the straight line 441, the region 452, and the like are different from those in FIGS. 15A and 15B.

In addition, in FIG. 21, the components having the same symbols as those in FIG. 19 are denoted by the same symbols.

Herein, in Comparative Example C, the conditions (C1) and (C2) described above will be considered.

(C1) On the radially outside the centroid G in the region 452 (the left side in FIG. 21), since there is no equivalent to the contact portion 401b illustrated in FIG. 19, (C1) does not hold.

(C2) In the region 452, since the contact portion 401b illustrated in FIG. 19 does not exist, (C2) does not hold.

Modifications

Figure 22B:
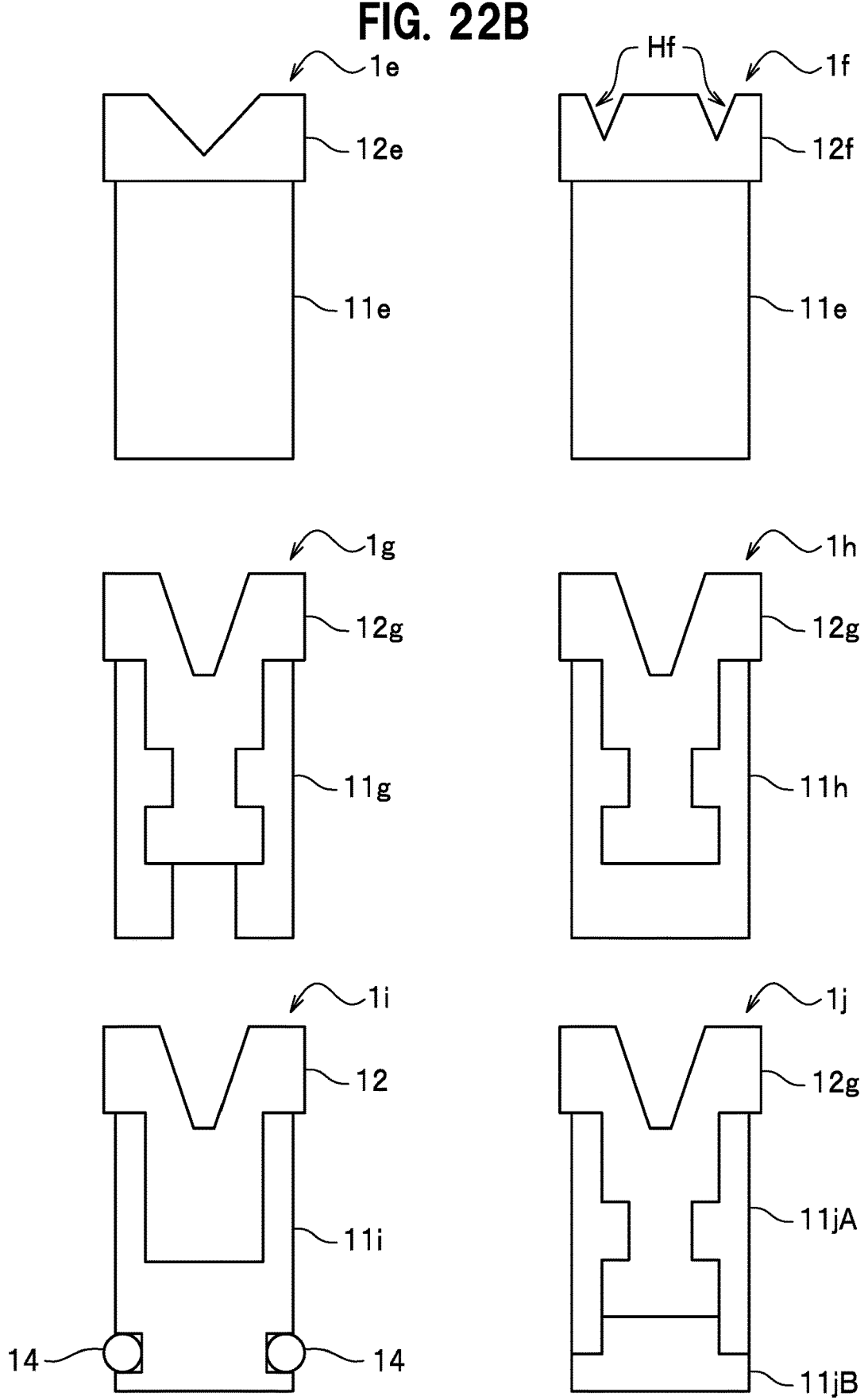
FIG. 22B is a diagram (part 2) illustrating modifications of the piston 1 according to this embodiment.

FIGS. 22A and 22B are cross-sectional views illustrating modifications of the piston 1 according to this embodiment. In FIGS. 22A and 22B, the upper side is the electrophoresis medium Q side, and the lower side is the plunger 61 side. In FIGS. 22A and 22B, elements having the same shape are denoted by the same symbols, and description thereof is omitted.

As in a piston 1a illustrated in FIG. 22A, a hollow Ha of a soft portion 12a may have a triangular pyramid shape (the cross section is triangular). In addition, like the piston 1a, a structure in which the depth of the hollow Ha is deeper than that of the piston 1 illustrated in FIGS. 6 and 7 may be employed.

The rigid portion 11 of the piston 1 illustrated in FIGS. 6 and 7 has a cylindrical shape, but a rigid portion 11b of a piston 1b or the like may have a bottomed cylindrical shape. Then, the soft portion 12a may be in contact with not only the upper surface of the cylindrical portion of the rigid portion 11b but also the inner bottom surface of the rigid portion 11b. Although the rigid portion 11b has a bottomed cylindrical shape, it can be easily injection molded.

Like a piston 1c, a bottom surface of a hollow Hc of a soft portion 12c may be closer to the electrophoresis medium Q than the uppermost surface of a rigid portion 11b. In other words, a structure in which the depth of the hollow Hc is shallow may be adopted.

Further, like a piston 1d, the rigid portion 11b may have a bottomed cylindrical shape, and the hollow H may have a bottom surface as that of the piston 1 in FIGS. 6 and 7.

Hereinafter, FIG. 22B will be referred.

Like a piston 1e, a rigid portion 11e may be cylindrical. In this case, a soft portion 12e has a structure mounted on an upper surface of a rigid portion 11e. In this case, it is desirable that both components be joined by an adhesive or the like.

In addition, like a piston 1f, a hollow Hf of a soft portion 12f may have a groove shape.

A piston 1g has a rigid portion 11g of which inner surface has a protrusion added to the inner surface of the rigid portion 11 of the piston 1 illustrated in FIGS. 6 and 7. A soft portion 12g is configured to match the shape of the inner surface of the rigid portion 11g. With such a configuration, the soft portion 12g can be fitted into the rigid portion 11g, and the soft portion 12g can be prevented from easily coming off the rigid portion 11g without fixing the both with an adhesive or the like. Since the soft portion 12g is soft, the soft portion 12g is fitted into the rigid portion 11g by pushing to be inserted into the rigid portion 11g through the top opening of the rigid portion 11g. In other words, for example, even if the electrophoresis medium Q becomes negative pressure (pressure lower than the atmospheric pressure) and a force is generated such that the piston 1g is pulled toward the electrophoresis medium Q (the upper side in FIG. 22B), the soft portion 12g and the rigid portion 11g are not separated.

In addition, a piston 1h has a rigid portion 11h which is the rigid portion 11g with a bottom added.

A piston 1i is the piston 1d with an O-ring 14 provided on a lower outer surface of a rigid portion 11i. If the soft portion 12 is made of silicon or the like, there is a possibility that water vapor or the like may be transmitted through the soft portion 12. Therefore, with the rubber O-ring 14 on the outer periphery of the rigid portion 11i, leakage of water vapor can be prevented. Moreover, with such a configuration, even if the electrophoresis medium Q leaks from the gap between the soft portion 12 and the outer cylinder 202 (see FIGS. 8A and 8B), the O-ring 14 functions as a second seal portion. Therefore, it is possible to prevent the electrophoresis medium Q from leaking out of the syringe 20. Alternatively, it is possible to efficiently prevent dust or the like entering from the outside from being mixed into the electrophoresis medium Q.

In the pistons 1b to 1f, and 1h to 1i except for the pistons 1a and 1g in FIGS. 22A and 22B, the rigid portions 11b, 11e, 11h, 11i, and 11jA, with 11jB adopt a bottomed cylindrical shape or a cylindrical shape, which has the following two effects. First, at least at the time of pressing the electrophoresis medium Q, not only the outer peripheral portions of the soft portions 12, 12a, 12c, and 12e to 12g but also the central bottom portions of the soft portions 12, 12a, 12c, and 12e to 12g are respectively in contact with and supported by the rigid portions 11b, 11e, 11h, 11i, and 11jA, with 11jB. Therefore, it is possible to minimize deformation of the soft portions 12, 12a, 12c, and 12e to 12g in a direction toward the plunger 61 (the downward direction in FIGS. 22A and 22B) when a high pressure is applied to the electrophoresis medium Q. With this configuration, the deformation of the soft portions 12, 12a, 12c, and 12e to 12g in the radially outside direction (the left and right directions in FIGS. 22A and 22B) can be enhanced. In addition, it is possible to prevent the soft portions 12, 12a, 12c, and 12e to 12g from being broken by excessive deformation of the soft portions 12, 12a, 12c, and 12e to 12g toward the plunger 61. Second, in a case where the bottom surface of the rigid portion 11 is not closed, and the tip diameter of the plunger 61 is small, there is a risk that the tip of the plunger 61 enters the rigid portion 11 and directly pushes up the bottom surface of the soft portion 12. By adopting a bottomed cylindrical shape or a cylindrical shape like the rigid portions 11b, 11e, 11h, 11i, and 11jA, with 11jB, the risk can be avoided.

On the other hand, it is generally difficult to injection mold a configuration such as the rigid portion 11h of a syringe 1h, in which both the bottomed cylindrical shape and the protrusion on the inner wall coexist. A syringe 1j illustrates a configuration example for solving this problem. In other words, the rigid portion 11h of the syringe 1h is divided into two parts, the rigid portion 11jA and the rigid portion 11jB. The rigid portion 11jA and the rigid portion 11jB can be separately manufactured by injection molding. The same configuration as that of the rigid portion 11h is obtained by inserting the manufactured rigid portion 11jB into the manufactured rigid portion 11jA. Incidentally, the connection between the rigid portion 11jA and the rigid portion 11jB does not need to be so strong. This is because, when pressurized, the plunger 61 pushes up the bottom surface of the rigid portion 11jB, so even if the electrophoresis medium Q has a high pressure and a force to push down the soft portion 12g is generated, the rigid portion 11jB is not separated from the rigid portion 11jA. In addition, in a case where the electrophoresis medium Q becomes a negative pressure, a force is generated that pulls up the soft portion 12g of the syringe 1j. However, since this force does not directly act on the rigid portion 11jB, the connection between the rigid portion 11jA and the rigid portion 11jB need not to be so strong.

The inventors used the piston 1 of this embodiment for the syringe 20 illustrated in FIGS. 1 to 5. Herein, the piston 1 was the piston 1 illustrated in FIGS. 6 and 7. The syringe 20 including the piston 1 was disposable, and the contained separation medium for 10 analyses was discarded after consumption.

Further, the plunger 61 was made of metal. The plunger 61 was attachable to and detachable from the piston 1. The plunger 61 was configured not to be disposable.

After the syringe 20 is attached to the capillary electrophoresis device W, as described above, the plunger 61 pushes up the piston 1 so that the electrophoresis medium Q is sent to each capillary Ca. At this time, a pressure of several tens of atmospheres is applied to the electrophoresis medium Q.

By using the piston 1 of this embodiment, the syringe 20 having high pressure resistance performance and stable liquid feeding performance can be manufactured at a low cost and can be disposable.

[Applications]

Next, applications of the piston 1 of this embodiment will be described with reference to FIGS. 23 to 25.

(First Application)

Figure 23:
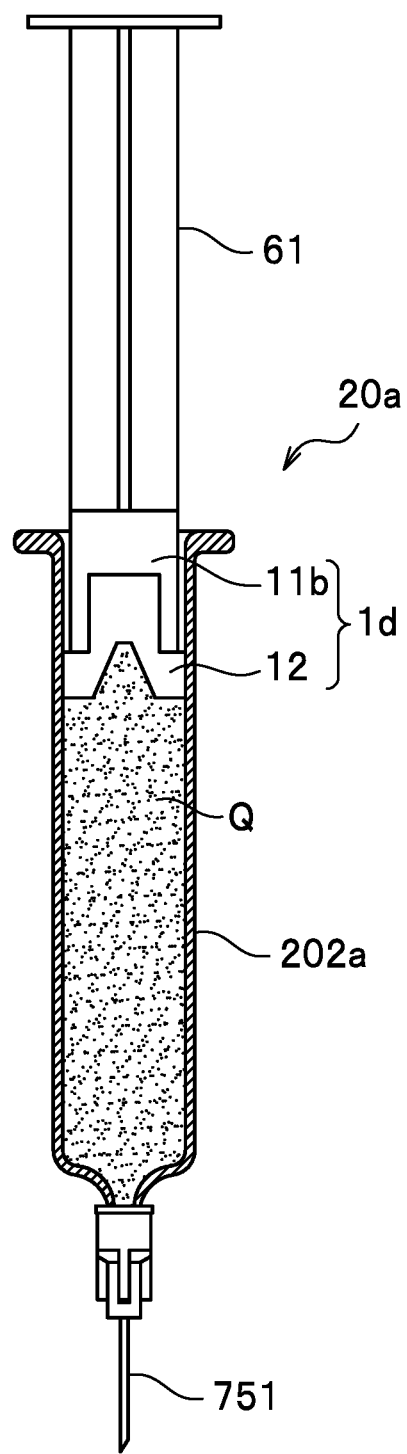
FIG. 23 is an example in which the piston 1 according to this embodiment is used as a syringe 20a for sample injection in a gas chromatography.

FIG. 23 is a cross-sectional view of a syringe 20a. The syringe 20a has a plastic outer cylinder 202a unlike a gas-tight syringe such as a Hamilton syringe used for sample injection in gas chromatography has a glass outer cylinder.

In FIG. 23, the piston 1d illustrated in FIG. 22A is used. Of course, the piston 1 illustrated in FIGS. 6 and 7 and the pistons 1a to 1c and 1e to 1j illustrated in FIGS. 22A and 22B may be used. However, the rigid portion 11b and the plunger 61 are integrated. A metal needle 751 is connected to the tip of the syringe 20a.

The soft portion 12 of the piston 1d is made of silicon rubber having a hardness of 50 degrees, and can be manufactured at a low cost by injection molding. The outer cylinder 202a, the rigid portion 11b, and the plunger 61 were made of polypropylene, and also manufactured at a low cost by injection molding.

The outer cylinder 202a had an inner diameter of 5 mm and a total length of 80 mm. The outer diameter of the soft portion 12 at the convex portion 13 (see FIGS. 6 and 7) was 5.3 mm when the soft portion 12 was not inserted into the outer cylinder 202a. Meanwhile, the outer diameter of the rigid portion 11 was 4.9 mm. At this time, the outer diameter of the rigid portion 11 is 98% of the inner diameter of the outer cylinder 202a.

When the plunger 61 was pushed with 2-kgf force with a finger, with the tip of the syringe 20a containing the electrophoresis medium Q closed, a pressure of slightly more than 10 atmospheres (more than 1 MPa) was generated, but a leak of the electrophoresis medium Q did not occur.

Next, instead of the electrophoresis medium Q, the syringe 20a filled with a gas sample was used. As a result, a gas sample was successfully injected into a gas chromatography device (not illustrated), and a proper analysis result was obtained.

(Second Application)

Figure 24:
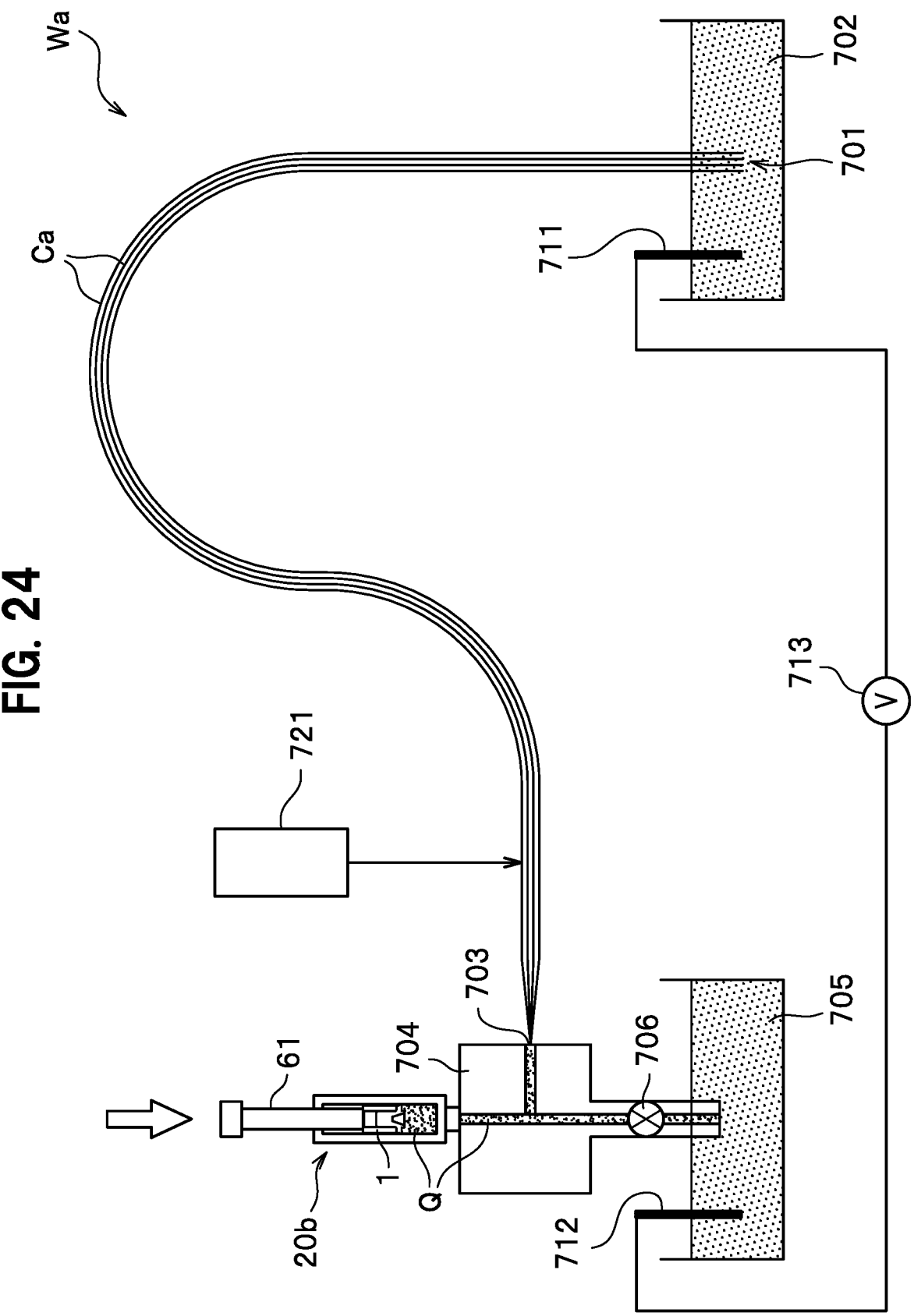
FIG. 24 is a diagram illustrating an example in which the piston 1 of this embodiment is used for a capillary electrophoresis device Wa.

FIG. 24 is a diagram illustrating an example in which the piston 1 of this embodiment is used for a capillary electrophoresis device Wa of a different type from those in FIGS. 1 and 2.

In the capillary electrophoresis device Wa, sample injection ends 701 of a plurality of capillaries Ca (four capillaries Ca are illustrated in FIG. 24) are immersed in a cathode buffering liquid 702, and sample elution ends 703 are connected to a pump block 704. The pump block 704 and a syringe 20b are connected, and the insides of both are filled with the electrophoresis medium Q. When a valve 706 of the pump block 704 is opened, the sample elution ends 703 are electrically connected to an anode buffering liquid 705 via the electrophoresis medium Q inside the pump block 704. With the valve 706 of the pump block 704 closed, when the plunger 61 of the syringe 20b is pushed down in the direction of the outlined arrow, the piston 1 is also pushed down. As a result, the electrophoresis medium Q inside the syringe 20b and the electrophoresis medium Q inside the pump block 704 are pressurized. The pressurized electrophoresis medium Q is filled into each capillary Ca from the sample elution end 703 toward the sample injection end 701.

After filling, when the valve 706 is opened, the cathode buffering liquid 702 and the anode buffering liquid 705 are electrically connected via the electrophoresis medium Q inside the plurality of capillaries Ca and the electrophoresis medium Q inside the pump block 704. After each different sample is injected from each sample injection end 701 into each capillary Ca, a constant high voltage is applied across a cathode electrode 711 immersed in the cathode buffering liquid 702 and an anode electrode 712 immersed in the anode buffering liquid 705 by a high voltage power source 713. Thus, each sample is electrophoresed from the sample injection end 701 toward the sample elution end 703. In addition, a detection unit 721 performs laser-induced fluorescence detection at a position where the sample is electrophoresed by a certain distance in each capillary and analyses each sample.

A gas-tight syringe made of glass has been used as the conventional syringe as in the first application illustrated in FIG. 23 so far. On the contrary, a syringe 20b made of plastic, manufacturable at low cost, and equivalent to the syringe 20a in FIG. 23 is used. In other words, the syringe 20b is obtained by removing the needle 751 from the syringe 20a in FIG. 23. By mechanically pressing down the plunger 61 and the piston 1 in the direction of the outlined arrow, a high pressure of several tens of atmospheres is applied to the internal electrophoresis medium Q, and the electrophoresis medium Q is injected into the plurality of capillaries Ca from the sample elution ends 703 to fill the capillaries towards the sample injection ends 701.

Since the syringe 20b and the piston 1 have high pressure resistance performance, no leakage of the electrophoresis medium Q occurs, and the electrophoresis medium Q is successfully filled in the capillaries Ca. A portion (the soft portion 12) of the piston 1 in contact with the electrophoresis medium Q is made of rubber, and has high elasticity. Therefore, even when the filling operations were repeatedly performed, the tip of the piston 1 does not wear, and the pressure resistance performance is maintained for a long period of time. By using the syringe 20b made of plastic, including the piston 1 of this embodiment, the initial cost and the maintenance cost can be significantly reduced.

On the other hand, although conventional gas-tight syringes made of glass have pressure resistance performance of several tens of atmospheres (several MPa), such syringes are expensive, and the pressure resistance performance is lost due to wearing of the piston tip. Thus, it is necessary to change the syringe regularly. As described above, these problems are solved by using the piston 1 of this embodiment.

(Third Application)

Figure 25:
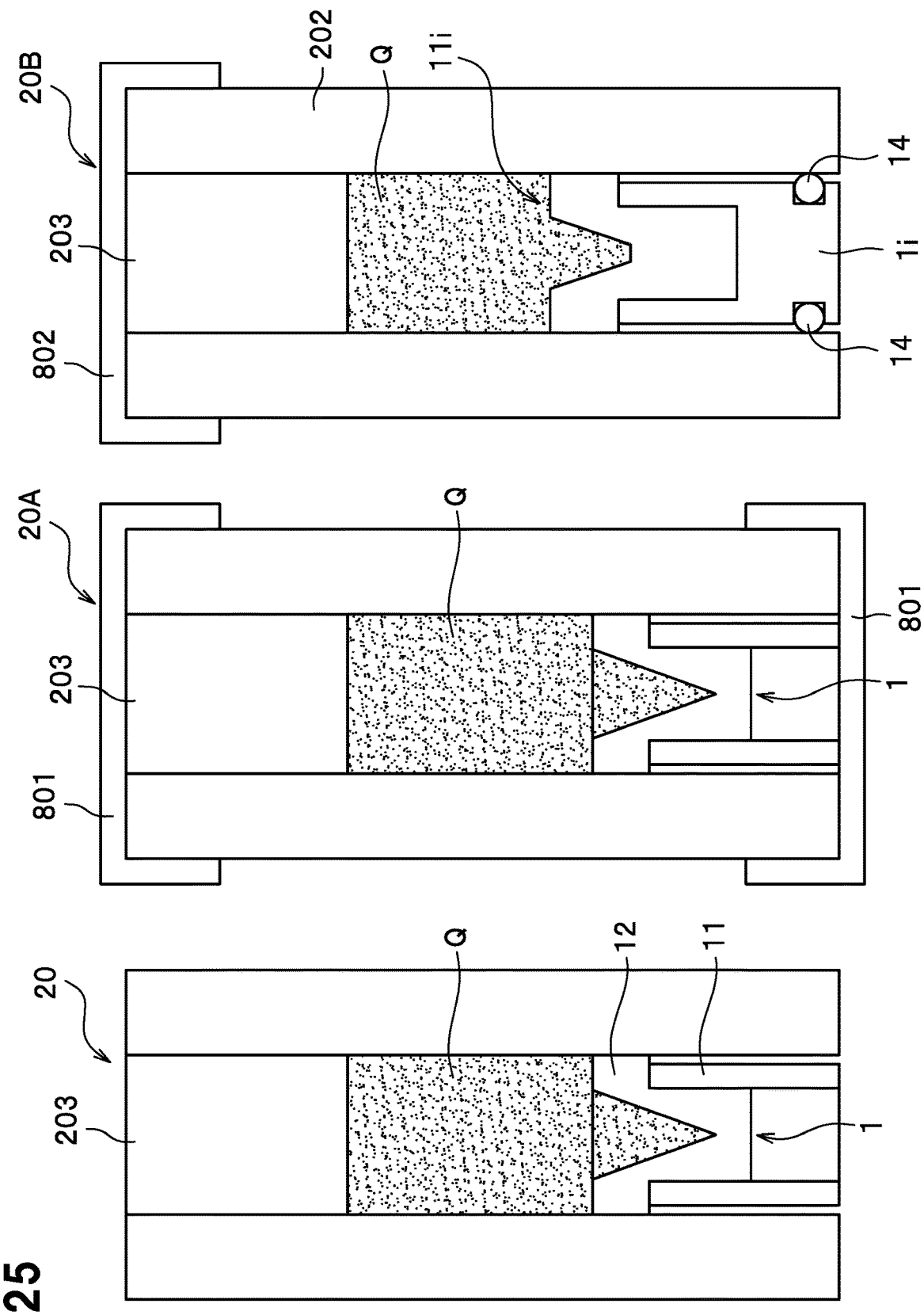
FIG. 25 is a diagram illustrating examples of transport and storage of the syringe 20 using the piston 1 of this embodiment.

FIG. 25 is a diagram illustrating an example of transportation and storage of the syringe 20 using the piston 1 of this embodiment.

The syringe 20, with being filled with a liquid such as the electrophoresis medium Q and sealed with the piston 1 and the rubber stopper 203, is sold, transported, and stored. The syringe 20 in this state corresponds to the syringe 20 in FIG. 3 with the piston 1A replaced by the piston 1 and before being set on the guide 101 (see FIG. 3 and the like). Here, the rubber stopper 203 in FIG. 25 has a shape different from those in FIGS. 3 to 5 and is simply depicted. In addition, in FIG. 25, the cap 204 (see FIGS. 3 to 5) is not illustrated.

The syringe 20 is an example in which the piston 1 of this embodiment is used as a piston.

When silicon rubber is used as the material of the soft portion 12 of the piston 1 in the syringe 20 and is distributed as a consumable, the following risks occur. That is, while the syringe 20 is transported or stored, there is a risk that the permeability of water vapor of the silicon rubber causes the concentration of the internal electrophoresis medium Q to be changed. A similar problem occurs to even a syringe 20 having the rubber stopper 203 made of silicon rubber.

In order to avoid such a risk, it may have a structure like a syringe 20A and a syringe 20B.

The end surface of the syringe 20A and the end surface of the rubber stopper 203 are sealed with members having a low permeability of water vapor, for example, aluminum sheets 801 or the like. Then, the user removes the aluminum sheets 801 immediately before use.

In the syringe 20B, the piston 1i in FIG. 22B is used. An O-ring 14 made of a rubber material having a low permeability of water vapor, for example, butyl rubber, is mounted on the outer surface of the rigid portion 11i, and the O-ring 14 is in contact with the inner wall of the outer cylinder 202. However, force of the O-ring 14 to contact the inner wall of the outer cylinder 202 is set to be smaller than that of the soft portion 12 to contact the inner wall the outer cylinder 202 (see FIG. 22B). This prevents the O-ring 14 from increasing the sliding resistance of the piston 1i. The O-ring 14 also has a function of preventing the internal electrophoresis medium Q from leaking to the outside if the internal electrophoresis medium Q leaks from the gap between the piston 1i and the inner wall of the outer cylinder 202. Similarly, the end surface of the rubber stopper 203 is also covered with a lid 802 made of a rubber material having a low permeability of water vapor, for example, butyl rubber.

(Fourth Application)

In a microchip electrophoresis apparatus, a user manually fills a channel with the electrophoresis medium Q using a plastic syringe. However, since the conventional plastic syringe does not have high pressure resistance performance, it is not possible to fill the highly viscous electrophoresis medium Q at a high pressure.

Therefore, with the use of the syringe 20a made of plastic (see FIG. 23) using the piston 1 of this embodiment, it is possible to improve the pressure resistance performance and to fill the electrophoresis medium Q having high viscosity manually and at a high pressure. For example, if the inner diameter of the syringe 20a is 1 mm, and the force for pressing the plunger 61 is 1 kgf, the pressure will be 100 atm (10 MPa). However, with the use of the piston 1 of this embodiment, it is possible to withstand this pressure. In this way, a high pressure of 10 MPa or more can be easily realized even by manual operation using the syringe 20 with the piston 1 of this embodiment.

Figure 26:
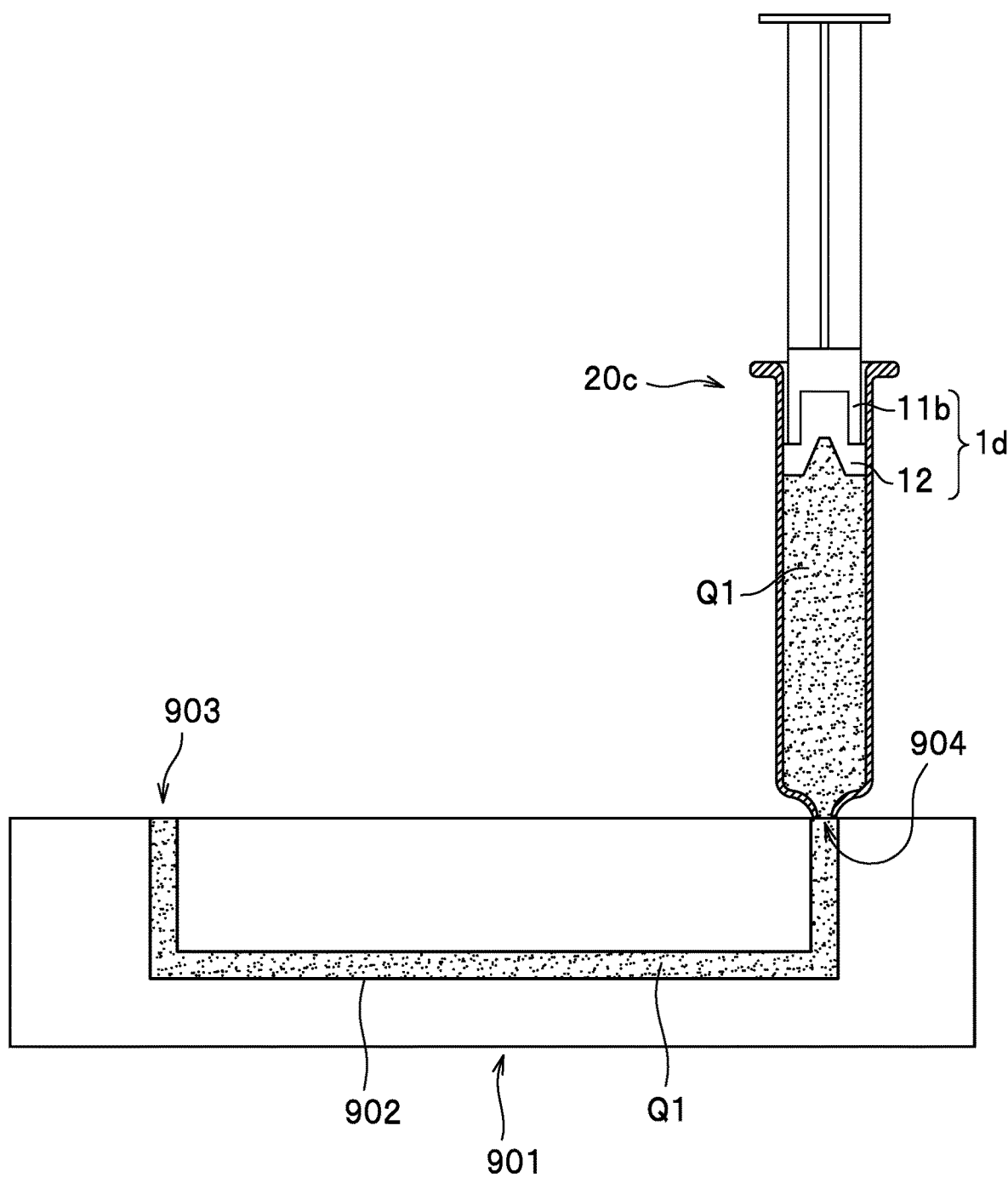
FIG. 26 is a diagram schematically illustrating a cross section of a microchip 901.

FIG. 26 is a diagram schematically illustrating a cross section of a microchip 901 for performing various analyses including electrophoresis.

One or a plurality of microchannels 902 are formed inside the microchip 901 (FIG. 26 illustrates a single microchannel 902). The microchannel 902 has an opening 903 and an opening 904, respectively. Since the microchannel 902 is fine, a high pressure is required to fill the inside with various analysis solutions Q1 including the separation medium. FIG. 26 illustrates a state where a syringe 20c filled with the analysis solution (medium) Q1 is connected to the opening 904. Further, the analysis solution Q1 corresponds to the electrophoresis medium Q so far. In this state, by pushing down the plunger 61 of the syringe 20c, a high pressure is applied to the analysis solution Q1 inside the syringe 20c, and the analysis solution Q1 is filled from the opening 904 toward the opening 903. Here, the syringe 20c is obtained by removing the needle 751 from the syringe 20a in FIG. 23.

In the above description, the syringe 20 (20a to 20c) has a cylindrical shape. However, the inner surface of the syringe 20 only needs to be cylindrical, and the outer surface of the syringe 20 may have any shape.

Figure 27:
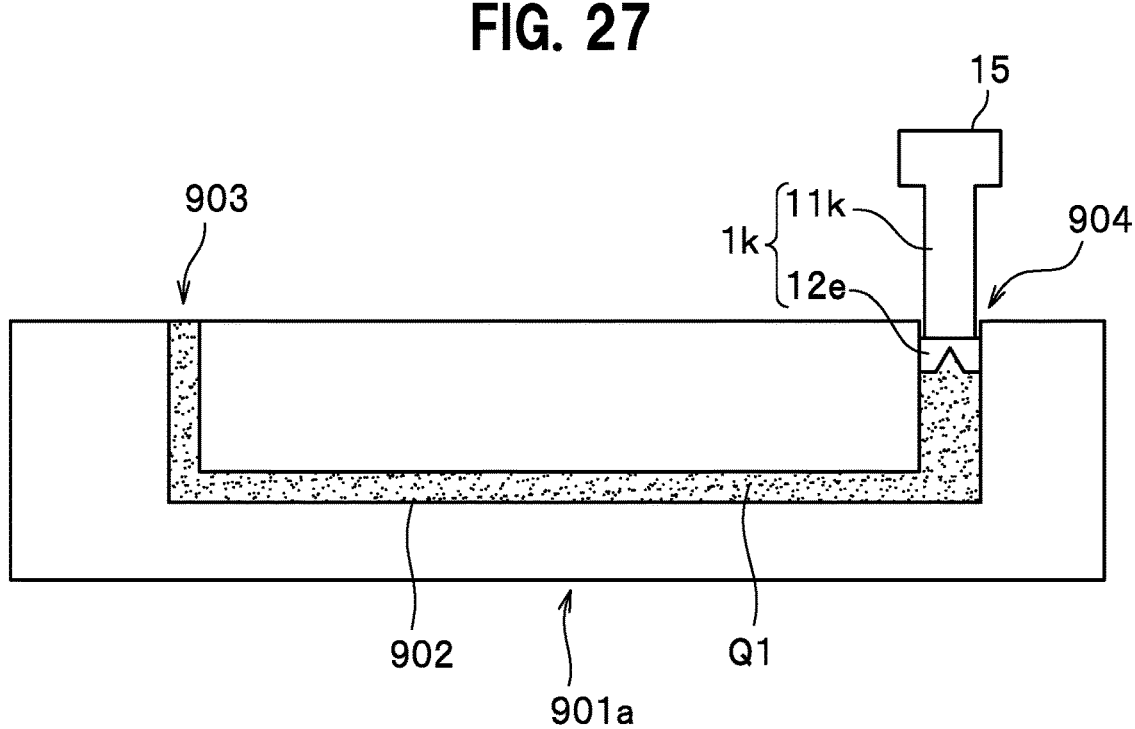

FIG. 27 is a diagram schematically illustrating a cross section of another microchip 901a different from that in FIG. 26. In FIG. 27, the same components as those in FIG. 26 are denoted by the same symbols, and the description thereof will be omitted.

The microchip 901a illustrated in FIG. 27 illustrates an example in which a piston 1k is embedded in an opening 904 of a microchannel 902, and the vicinity of the opening 904 itself functions as the syringe 20 (see FIGS. 8A and 8B). In other words, the microchip 901a itself corresponds to the syringe 20. Herein, the microchannel 902 is filled with the electrophoresis medium Q. Further, in FIG. 27, the piston 1k with the rigid portion 11k is the piston 1e in FIG. 22B with the rigid portion 11e provided with a pushing portion 15 for pushing by a user. Of course, the piston 1 of FIGS. 6 and 7 and the pistons 1a to 1j of FIGS. 22A and 22B may be used, and the pistons 1, 1a to 1d, and 1f to 1j provided with the pushing portions 15 may be used.

As described above, the microchip 901a itself corresponds to the syringe 20. Here, the inner surface of the syringe 20 has the cylindrical shape of the microchannel 902, but the outer surface of the syringe 20 has the shape of the microchip 901a. By using the piston 1k, not only can a high pressure be applied to the inside of the syringe 20, but also the entire analysis system (not illustrated) using the microchip 901a can be reduced in size.

(Fifth Application)

The piston 1 of this embodiment can be used as a syringe for the liquid dispensing device described in FIGS. 8 to 10 of Japanese Patent No. 4890670. The piston 1 of this embodiment can be used for applications requiring high pressure, such as a case where a highly viscous liquid (the electrophoresis medium Q) is sent to a narrow flow path. Further, the piston 1 of this embodiment is durable because the deterioration due to wear is small. Therefore, the number of replacements can be reduced, and the replacement cost can be reduced.

By using the piston 1 of this embodiment, the syringes 20 and 20a made of plastic and having a high pressure resistance performance of at least 0.1 MPa or more, preferably 1 MPa or more, more preferably 10 MPa or more (FIGS. 3 to 5, 8A, 8B, and 23) can be provided at a low cost. In particular, it is possible to realize high pressure resistance performance and low leakage with small sliding resistance by using the syringe 20 having an inner diameter of 10 mm or less, more preferably 5 mm or less.

(Sixth Application)

Figure 28:
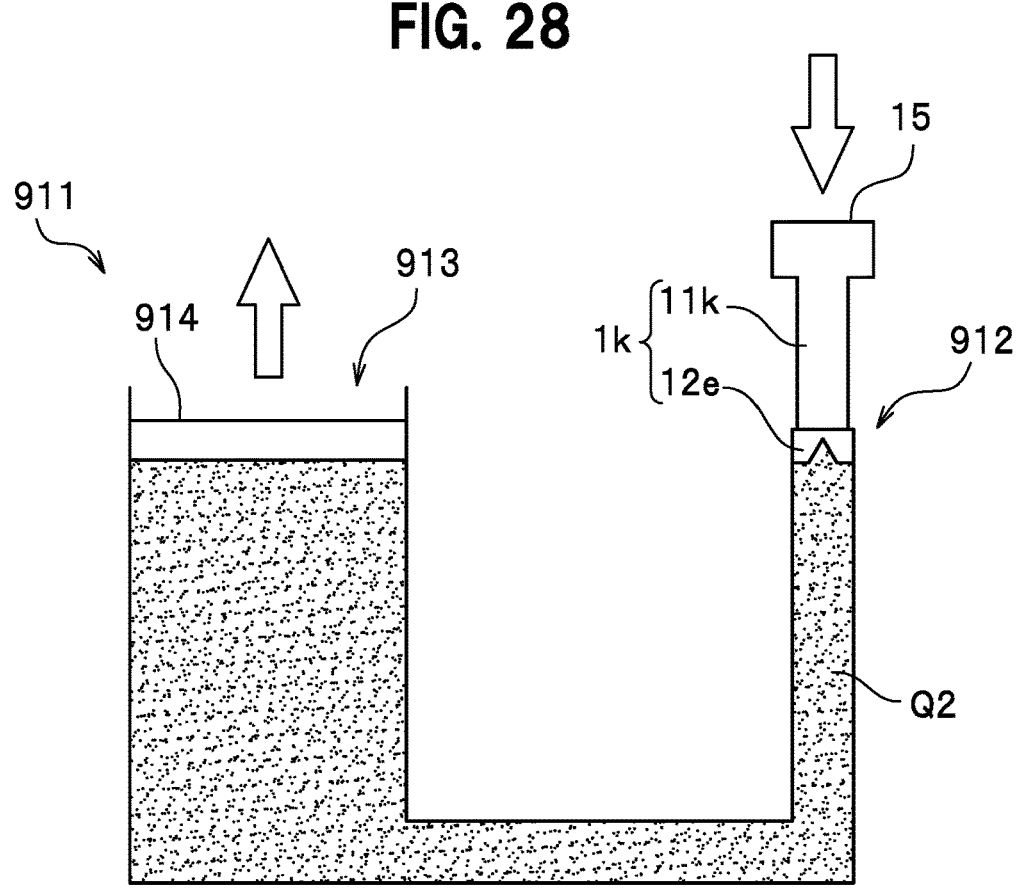
FIG. 28 is a diagram illustrating a hydraulic pump 911 for which the piston 1 of this embodiment is used.

FIG. 28 is a diagram illustrating a hydraulic pump 911 for which the piston 1k of this embodiment is used. As illustrated in FIG. 28, in the hydraulic pump 911 filled with an oil (medium) Q2, the piston 1k is mounted on an oil end surface 912 in the small-outer-diameter cylinder on the right side, and a driving object 914 is mounted on an oil end surface 913 in the large-outer-diameter cylinder on the left side. The oil Q2 corresponds to the electrophoresis medium Q described so far. Further, in FIG. 28, the piston 1k having the rigid portion 11k is the piston 1e having the rigid portion 11 in FIG. 22B with the pushing portion 15 for pushing by the user provided. Of course, the piston 1 of FIGS. 6 and 7 and the pistons 1a to 1j of FIGS. 22A and 22B may be used, and the pistons 1, 1a to 1d, and 1f to 1j provided with the pushing portions 15 may be used.

In this state, when the piston 1 is pushed to the downward direction (open arrow), the internal oil Q2 becomes in a high pressure state. Then, a very large upward force in accordance with the area ratio of the oil end surface 913 to the oil end surface 912 acts on the driving object 914 upward. Even in such an application, the piston 1k, which can be obtained at a low cost, maintains the sealing performance and can fulfill the purpose.

In the above, the case where the syringe 20 (20a to 20c) or the outer cylinder 202 (202a) is configured to be robust has been mainly described, but such a configuration is not necessarily required.

Figure 29A:
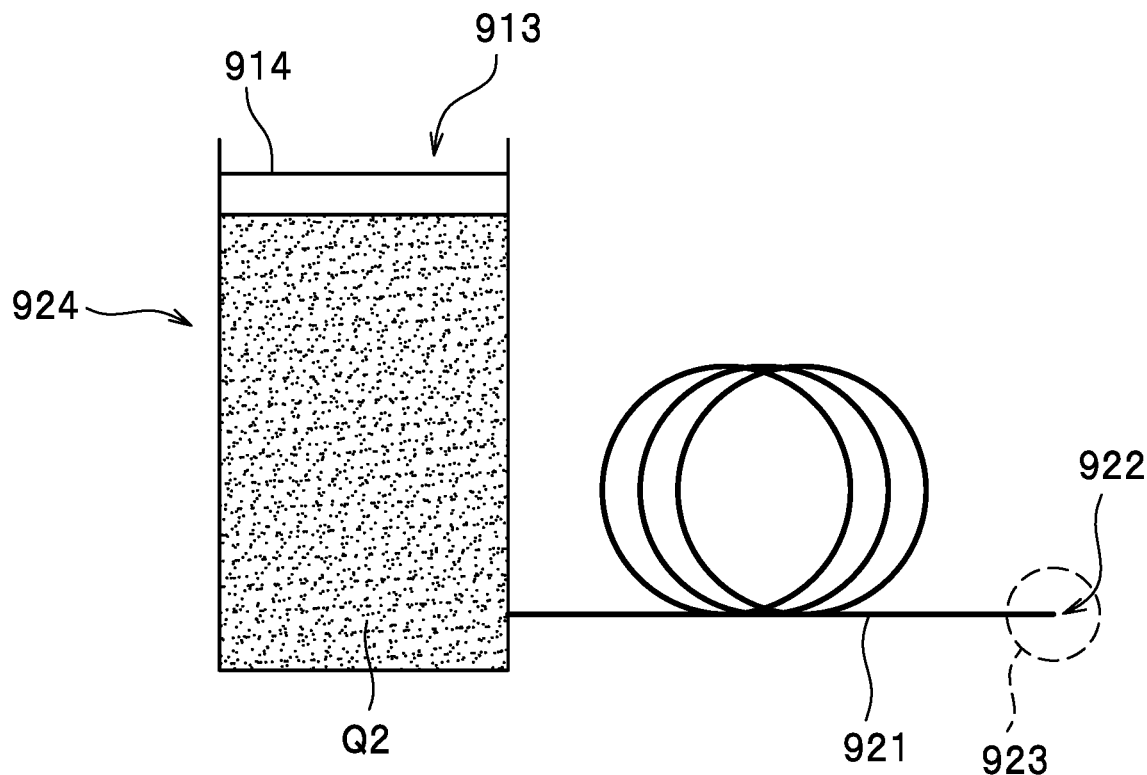
FIG. 29A is a diagram for describing a case where a tube 921 is used in place of the syringe 20.

FIG. 29A is a diagram for describing a case where a tube 921 which has pressure resistance but is flexible is used instead of the outer cylinder 202 (202a) of the syringe 20.

Figure 29B:
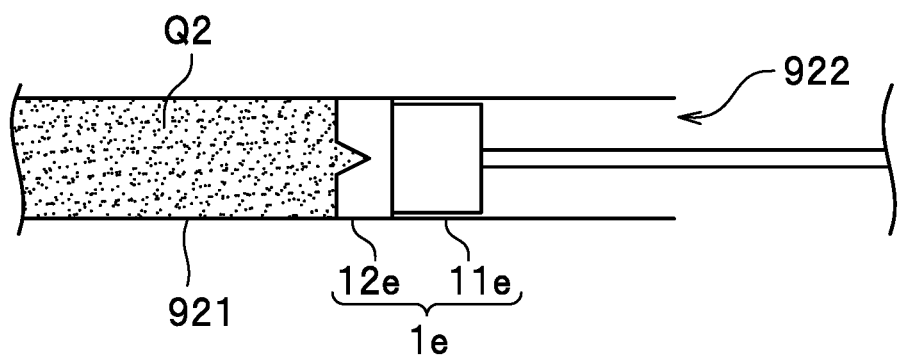
FIG. 29B is an enlarged view of an end portion 922 of the tube 921.

FIG. 29B is an enlarged view (Symbol 923) near an end portion 922 of the tube 921 to which the piston 1e is mounted.

As illustrated in FIG. 29A, the tube 921 which is flexible (for example, a PEEK tube) is connected to an oil container 924. The tube 921 and the oil container 924 are filled with the oil Q2. As described above, the oil Q2 corresponds to the electrophoresis medium Q. In addition, as illustrated in FIG. 29B which is an enlarged view of Symbol 923 in FIG. 29A, the piston 1e is mounted on the end portion 922 of the tube 921. Further, as illustrated in FIG. 29A, an oil end surface 913 in the oil container 924 has the same configuration as the oil end surface 913 in FIG. 28, and the driving object 914 is mounted on the oil end surface 913. In addition, in FIGS. 29A and 29B, the piston 1e illustrated in FIG. 22B is used. Of course, the piston 1 illustrated in FIGS. 6 and 7 and the pistons 1a to 1d and 1f to 1j illustrated in FIGS. 22A and 22B may be used. The inside of the tube 921 is filled with the oil Q2 so that air does not enter. Then, similarly to FIG. 28, when the piston 1e at the end portion 922 is pushed, a driving force that is many times the pushing force of the piston 1e can be obtained on the oil end surface 913.

Further, the present invention is not limited to the above embodiments, but various modifications may be contained. For example, the above-described embodiments of the invention have been described in detail in a clearly understandable way, and are not necessarily limited to those having all the described configurations.

In this embodiment, the medium (for example, the electrophoresis medium Q) in the syringe 20 is ejected from the syringe 20 when the piston 1 slides in the syringe 20, but the piston 1 slides in the syringe 20, so that a medium (such as the electrophoresis medium Q) may be sucked into the syringe 20.

In addition, in this embodiment, it is assumed that the deepest portion of the hollow H is located on the central axis T of the soft portion 12, but the invention is not limited thereto, and the deepest portion of the hollow H may be located at a position shifted from the central axis T of the soft portion 12. In addition, in the piston if in FIG. 22B, the hollow Hf forms a single ring-shaped groove, but the invention is not limited thereto, and a double or triple groove may be formed.

REFERENCE SIGNS LIST 1, 1a to 1k piston
11, 11b, 11e, 11g to 11i, 11jA, 11jB, 11k rigid portion
12, 12a, 12c, 12e, 12g soft portion
13 convex portion
14 O-ring
20, 20a, 20b, 20c, 20A, 20B syringe
61 plunger
202 outer cylinder (cylinder)
402 region (first region)
432 region (second region)
452 region (third region)
H hollow
Q electrophoresis medium (medium)
Q1 analysis solution (medium)
Q2 oil (medium)

The invention claimed is:

1. A piston which divides a space inside a cylinder into two parts, and slides inside the cylinder to pressurize or depressurize a medium made of liquid or gas stored in one space of the two parts, comprising:
   a soft portion; and
   a rigid portion having rigidity higher than rigidity of the soft portion,
   wherein the soft portion and the rigid portion are connected in series in a central axis direction of the cylinder such that the soft portion is in contact with the medium, and the rigid portion is not in contact with the medium,
   the soft portion does not cover an outer surface of the rigid portion at least when not in a pressurized state,
   the soft portion has a hollow on a surface in contact with the medium,
   the rigid portion has an end surface facing the soft portion, the end surface including at least an outer peripheral portion in contact with the soft portion,
   a maximum outer diameter which is the maximum outer diameter of the soft portion is larger than an outer diameter of the rigid portion,
   an outer diameter of the rigid portion at a contact portion with the soft portion is approximately the same as an outer diameter of the soft portion at a contact portion with the rigid portion, or the outer diameter of the rigid portion at the contact portion with the soft portion is smaller than the outer diameter of the soft portion at the contact portion with the rigid portion, so that an entire outer peripheral portion of the soft portion does not bend toward the rigid portion and the entire outer peripheral portion of the soft portion can be supported by the rigid portion when the soft portion moves toward the medium, and
   the maximum outer diameter of the soft portion is larger than the outer diameter of the rigid portion to the extent that the soft portion can be supported by the rigid portion when the soft portion moves toward the medium.

2. The piston according to claim 1, wherein
   a plunger to push the piston inside the cylinder is attachable to and detachable from the rigid portion.

3. The piston according to claim 1, wherein
   the cylinder is an outer cylinder of a syringe, and
   when the piston slides in the outer cylinder, the medium is sucked into the outer cylinder, or the medium is ejected from the outer cylinder.

4. The piston according to claim 3, wherein
   the soft portion and the rigid portion have a rotationally symmetric shape with respect to the central axis,
   the hollow has a shape that is rotationally symmetric with respect to the central axis, and
   when a direction from the rigid portion toward the soft portion is positive, in a longitudinal section of the soft portion including a deepest portion of the hollow and the central axis, a contact portion where the rigid portion and the soft portion are in contact with each other exists in a first region that is a region which is located in a radially outside direction of the soft portion from a position of the deepest portion of the hollow and in the positive direction from a position of the deepest portion.

5. The piston according to claim 4, wherein at least a part of the contact portion exists in a radially outside direction of the soft portion from a centroid of the first region.

6. The piston according to claim 4, wherein at least a part of the contact portion exists in the positive direction from the deepest portion of the hollow.

7. The piston according to claim 3, wherein
   the soft portion and the rigid portion have rotationally symmetric shapes with respect to the central axis,
   the hollow has a rotationally symmetric shape with respect to the central axis,
   when a direction from the rigid portion toward the soft portion is positive, in a longitudinal section of the soft portion including a deepest portion of the hollow and the central axis, a contact portion where the rigid portion and the soft portion are in contact with each other exists in a second region which is a region located in a radially outside direction of the soft portion from a position of the deepest portion of the hollow and located in the positive direction from a straight line which is perpendicular to the central axis and passes through a place in a most positive direction side in the contact portion, and
   at least a part of the contact portion exists in a radially outside direction of the soft portion from a centroid of the second region.

8. The piston according to claim 7, wherein at least a part of the contact portion exists in the positive direction from the deepest portion of the hollow.

9. The piston according to claim 3, wherein
   the soft portion and the rigid portion have rotationally symmetric shapes with respect to the central axis,
   the hollow has a rotationally symmetric shape with respect to the central axis,
   when a direction from the rigid portion toward the soft portion is positive, in a longitudinal section of the soft portion including a deepest portion of the hollow and the central axis, a contact portion where the rigid portion and the soft portion are in contact with each other exists in a third region that is a region which is located in a radially outside direction of the soft portion from a position of the deepest portion of the hollow, and at least a part of the contact portion exists in a radially outside direction of the soft portion from a centroid of the third region.

10. The piston according to claim 9, wherein at least a part of the contact portion exists in the positive direction from the deepest portion of the hollow.

11. The piston according to claim 3, wherein an O-ring is provided around the rigid portion.

12. A syringe containing a piston which includes a soft portion and a rigid portion having rigidity higher than rigidity of the soft portion, and in which the soft portion and the rigid portion are connected in series, wherein the syringe contains a liquid or gas medium which is pressurized or depressurized by sliding of the piston, the piston is arranged such that the soft portion is in contact with the medium, and the rigid portion is not in contact with the medium, the soft portion does not cover an outer surface of the rigid portion at least when not in a pressurized state, the soft portion includes a hollow on a surface in contact with the medium, the rigid portion is in contact with the soft portion at least at an outer peripheral portion and at an end surface facing the soft portion, a maximum outer diameter which is the maximum outer diameter of the soft portion is larger than an outer diameter of the rigid portion, the outer diameter of the rigid portion at a contact portion with the soft portion is approximately the same as an outer diameter of the soft portion at a contact portion with the rigid portion, or the outer diameter of the rigid portion at the contact portion with the soft portion is smaller than the outer diameter of the soft portion at the contact portion with the rigid portion, so that an entire outer peripheral portion of the soft portion does not bend toward the rigid portion and the entire outer peripheral portion of the soft portion can be supported by the rigid portion when the soft portion moves toward the medium, the maximum outer diameter of the soft portion is larger than the outer diameter of the rigid portion to the extent that the soft portion can be supported by the rigid portion when the soft portion moves toward the medium.

13. The syringe according to claim 12, wherein a plunger which is inserted into the syringe and pushes the rigid portion and that is attachable to and detachable from the rigid portion exists as a separate body from the syringe.

14. The piston according to claim 1, wherein when the outer diameter of the rigid portion is m and an inner diameter of the cylinder is M, a relationship of $0.9*M \leq m \leq M$ is satisfied.

* * * * *